(12) United States Patent
Highley et al.

(10) Patent No.: US 9,849,027 B2
(45) Date of Patent: Dec. 26, 2017

(54) OCULAR IMPLANTATION DEVICE

(75) Inventors: Brian Highley, Keller, TX (US);
Morgan Beeson, Irving, TX (US);
Randy Jackson, Irving, TX (US);
Christopher Edward Wayman, Dallas, TX (US); Lance Shetler, Burleson, TX (US); Antonio Cutino, Cumming, GA (US); Michael Thomas Wright, Allen, TX (US)

(73) Assignee: Alimera Sciences, Inc., Alpharetta, GA (US)

( * ) Notice: Subject to any disclaimer, the term of this patent is extended or adjusted under 35 U.S.C. 154(b) by 0 days.

(21) Appl. No.: 12/266,699

(22) Filed: Nov. 7, 2008

(65) Prior Publication Data

US 2009/0281520 A1 Nov. 12, 2009

Related U.S. Application Data

(60) Provisional application No. 61/075,786, filed on Jun. 26, 2008, provisional application No. 60/986,464, filed on Nov. 8, 2007.

(51) Int. Cl.
*A61F 9/00* (2006.01)
*A61M 37/00* (2006.01)

(52) U.S. Cl.
CPC ........ *A61F 9/0017* (2013.01); *A61M 37/0069* (2013.01); *A61M 2210/0612* (2013.01)

(58) Field of Classification Search
CPC .... A61F 9/0008; A61F 9/0017; A61F 9/0026; A61M 31/007; A61M 37/0069; A61M 2210/0612

(Continued)

(56) References Cited

U.S. PATENT DOCUMENTS 842,631 A   1/1907  Deperdussin
3,220,413 A  11/1965 Sunnen
(Continued)

FOREIGN PATENT DOCUMENTS

EP   0 415 504   3/1991
EP   0 544 948   6/1993
(Continued)

OTHER PUBLICATIONS

International Search Report and Written Opinion of the International Searching Authority for International Application No. PCT/US2008/082735; International Filing Date: Nov. 7, 2008; Date of Completion: Jan. 6, 2009; dated Jan. 16, 2009.

(Continued)

*Primary Examiner* — Shefali Patel
(74) *Attorney, Agent, or Firm* — Brinks Gilson & Lione

(57) ABSTRACT

An ocular implantation device comprises a housing having a longitudinal axis, a needle configured to receive an implant, and a plunger and a rod operatively coupled together. The plunger and the rod are disposed in the housing and are collectively, translationally moveable along the longitudinal axis of the housing. The rod is configured to be receivable within at least a portion of the needle to enable the rod to move the implant therethrough. An actuator is operatively engaged with the plunger such that movement of the actuator in a direction aligned with the longitudinal axis of the housing results in the translational movement of the plunger and the rod along the longitudinal axis of the housing in order to deliver the implant through the needle to a target site. An alternative embodiment of an ocular implantation device uses a retractable needle to deliver an implant.

15 Claims, 14 Drawing Sheets

FIG. 3

(58) Field of Classification Search
USPC .................. 604/506, 521, 60, 64, 57, 234
See application file for complete search history.

(56) References Cited

U.S. PATENT DOCUMENTS

| | | | |
|---|---|---|---|
| 3,238,941 A | 3/1966 | Klein et al. | |
| 3,698,390 A | 10/1972 | Ferris | |
| 3,921,632 A | 11/1975 | Bardani | |
| 3,937,370 A | 2/1976 | Witty | |
| 4,077,406 A | 3/1978 | Sandhage et al. | |
| 4,105,030 A | 8/1978 | Kercso | |
| 4,144,317 A | 3/1979 | Higuchi et al. | |
| 4,277,888 A * | 7/1981 | Szabo | B26B 5/002 30/162 |
| 4,447,223 A | 5/1984 | Kaye et al. | |
| 4,451,254 A | 5/1984 | Dinius et al. | |
| 4,597,753 A | 7/1986 | Turley | |
| D287,879 S | 1/1987 | Braxton et al. | |
| 4,659,326 A | 4/1987 | Johnson et al. | |
| 4,668,506 A | 5/1987 | Bawa | |
| 4,715,373 A | 12/1987 | Mazzocco et al. | |
| 4,759,359 A | 7/1988 | Willis et al. | |
| 4,799,478 A | 1/1989 | Fedorov et al. | |
| 4,850,970 A | 7/1989 | Sutherland | |
| 4,853,224 A | 8/1989 | Wong | |
| 4,900,304 A * | 2/1990 | Fujioka | A61M 37/0069 604/242 |
| 4,907,587 A | 3/1990 | Fedorov et al. | |
| 4,915,686 A | 4/1990 | Frederick | |
| 4,919,130 A | 4/1990 | Stoy et al. | |
| 4,955,889 A | 9/1990 | Van Gent | |
| 4,959,217 A | 9/1990 | Sanders et al. | |
| 4,997,652 A | 3/1991 | Wong | |
| 5,014,717 A | 5/1991 | Lohrmann | |
| 5,059,172 A | 10/1991 | Sutherland et al. | |
| 5,098,439 A | 3/1992 | Hill et al. | |
| 5,098,443 A | 3/1992 | Parel et al. | |
| 5,135,493 A | 8/1992 | Peschke | |
| 5,164,188 A | 11/1992 | Wong | |
| 5,178,635 A | 1/1993 | Gwon et al. | |
| 5,190,552 A | 3/1993 | Kelman | |
| 5,222,972 A | 6/1993 | Hill et al. | |
| 5,250,026 A | 10/1993 | Ehrlich et al. | |
| 5,279,554 A | 1/1994 | Turley | |
| 5,284,479 A | 2/1994 | de Jong | |
| 5,300,114 A | 4/1994 | Gwon et al. | |
| 5,336,206 A | 8/1994 | Shichman | |
| 5,378,475 A * | 1/1995 | Smith | A61F 9/0017 424/422 |
| 5,451,213 A | 9/1995 | Teicher et al. | |
| 5,466,233 A | 11/1995 | Weiner et al. | |
| 5,476,511 A | 12/1995 | Gwon et al. | |
| 5,494,484 A | 2/1996 | Feingold | |
| 5,499,987 A | 3/1996 | Feingold | |
| 5,562,676 A | 10/1996 | Brady et al. | |
| 5,582,613 A | 12/1996 | Brady et al. | |
| 5,584,304 A | 12/1996 | Brady | |
| 5,616,148 A | 4/1997 | Eagles et al. | |
| 5,620,450 A | 4/1997 | Eagles et al. | |
| 5,643,276 A | 7/1997 | Zaleski | |
| 5,653,753 A | 8/1997 | Brady et al. | |
| 5,725,521 A | 3/1998 | Mueller | |
| 5,735,858 A | 4/1998 | Makker et al. | |
| 5,776,138 A | 7/1998 | Vidal et al. | |
| 5,807,400 A | 9/1998 | Chambers et al. | |
| 5,810,833 A | 9/1998 | Brady et al. | |
| 5,824,001 A | 10/1998 | Erskine | |
| 5,824,072 A | 10/1998 | Wong | |
| D402,031 S | 12/1998 | Roberts et al. | |
| D402,757 S | 12/1998 | Davis et al. | |
| 5,876,373 A | 3/1999 | Giba et al. | |
| 5,921,989 A | 7/1999 | Deacon et al. | |
| 5,928,245 A | 7/1999 | Wolf et al. | |
| 5,941,250 A | 8/1999 | Aramant et al. | |
| 5,947,975 A | 9/1999 | Kikuchi et al. | |
| 5,947,976 A | 9/1999 | Van Noy et al. | |
| 5,957,892 A | 9/1999 | Thorne | |
| 6,010,510 A | 1/2000 | Brown et al. | |
| 6,051,000 A | 4/2000 | Heyman | |
| 6,074,397 A | 6/2000 | Chambers et al. | |
| 6,083,231 A | 7/2000 | Van Noy et al. | |
| 6,093,193 A | 7/2000 | Makker et al. | |
| 6,117,443 A | 9/2000 | Cherif-Cheikh | |
| 6,120,786 A | 9/2000 | Cherif Cheikh | |
| 6,129,733 A | 10/2000 | Brady et al. | |
| 6,142,972 A | 11/2000 | Cheikh | |
| 6,142,995 A | 11/2000 | Cosmescu | |
| 6,143,001 A | 11/2000 | Brown et al. | |
| D434,558 S | 12/2000 | Brady et al. | |
| 6,159,218 A | 12/2000 | Aramant et al. | |
| 6,179,843 B1 | 1/2001 | Weiler | |
| 6,190,350 B1 | 2/2001 | Davis et al. | |
| 6,203,549 B1 | 3/2001 | Waldock | |
| 6,231,603 B1 | 5/2001 | Lang et al. | |
| 6,238,433 B1 | 5/2001 | Portney | |
| 6,251,114 B1 | 6/2001 | Farmer et al. | |
| 6,267,768 B1 | 7/2001 | Deacon et al. | |
| 6,280,449 B1 | 8/2001 | Blake | |
| RE37,387 E | 9/2001 | Brady et al. | |
| 6,355,046 B2 | 3/2002 | Kikuchi et al. | |
| 6,375,972 B1 | 4/2002 | Guo et al. | |
| 6,398,789 B1 | 6/2002 | Capetan | |
| 6,413,245 B1 | 7/2002 | Yaacobi et al. | |
| 6,428,545 B2 | 8/2002 | Portney | |
| 6,439,276 B1 | 8/2002 | Wood et al. | |
| D463,555 S | 9/2002 | Etter et al. | |
| 6,447,519 B1 | 9/2002 | Brady et al. | |
| 6,447,520 B1 | 9/2002 | Ott et al. | |
| 6,503,275 B1 | 1/2003 | Cumming | |
| 6,558,395 B2 | 5/2003 | Hjertman et al. | |
| D475,785 S | 6/2003 | Chang | |
| 6,579,256 B2 | 6/2003 | Hughes | |
| 6,605,093 B1 | 8/2003 | Blake | |
| 6,699,285 B2 | 3/2004 | Zapata | |
| 6,723,104 B2 | 4/2004 | Ott | |
| 6,770,093 B2 | 8/2004 | Worst et al. | |
| 6,844,343 B1 | 1/2005 | Pfleiderer et al. | |
| 6,858,612 B1 | 2/2005 | Pfleiderer et al. | |
| D502,542 S | 3/2005 | Cohn et al. | |
| 6,899,717 B2 | 5/2005 | Weber et al. | |
| 6,923,815 B2 | 8/2005 | Brady et al. | |
| 6,936,053 B1 | 8/2005 | Weiss | |
| 6,960,196 B2 | 11/2005 | Prindle | |
| 7,090,681 B2 | 8/2006 | Weber et al. | |
| 7,097,649 B2 | 8/2006 | Meyer | |
| 7,118,552 B2 | 10/2006 | Shaw et al. | |
| 7,147,644 B2 | 12/2006 | Weber et al. | |
| 7,217,274 B2 | 5/2007 | Meyer | |
| 7,344,554 B2 | 3/2008 | Kuyava et al. | |
| D568,475 S | 5/2008 | Sandel et al. | |
| 2001/0001822 A1 | 5/2001 | Chambers et al. | |
| 2002/0026176 A1 | 2/2002 | Varner et al. | |
| 2002/0151904 A1 | 10/2002 | Feingold et al. | |
| 2002/0165610 A1 | 11/2002 | Waldock | |
| 2002/0173756 A1 | 11/2002 | Waldock | |
| 2003/0050647 A1 | 3/2003 | Brady | |
| 2003/0054023 A1 | 3/2003 | Hughes | |
| 2003/0078545 A1 | 4/2003 | Howie et al. | |
| 2003/0171723 A1 | 9/2003 | Ponzi | |
| 2003/0176870 A1 | 9/2003 | Ott | |
| 2003/0204252 A1 | 10/2003 | Paul et al. | |
| 2004/0054374 A1 | 3/2004 | Weber et al. | |
| 2004/0097778 A1 | 5/2004 | Hughett et al. | |
| 2004/0147938 A1 | 7/2004 | Dusek et al. | |
| 2004/0215133 A1 | 10/2004 | Weber et al. | |
| 2005/0033308 A1 | 2/2005 | Callahan et al. | |
| 2005/0048099 A1* | 3/2005 | Shiah | A61K 9/0051 424/428 |
| 2005/0101967 A1 | 5/2005 | Weber et al. | |
| 2005/0154399 A1* | 7/2005 | Weber | A61F 2/167 606/107 |
| 2005/0203542 A1 | 9/2005 | Weber et al. | |
| 2006/0004381 A1 | 1/2006 | Feingold et al. | |
| 2006/0211982 A1 | 9/2006 | Prestrelski et al. | |

(56) References Cited

U.S. PATENT DOCUMENTS

| | | |
|---|---|---|
| 2006/0235430 A1 | 10/2006 | Le et al. |
| 2006/0241650 A1 | 10/2006 | Weber et al. |
| 2007/0243230 A1 | 10/2007 | De Juan, Jr. et al. |
| 2007/0260201 A1 | 11/2007 | Prausnitz et al. |
| 2007/0260203 A1 | 11/2007 | Donello et al. |
| 2007/0287958 A1 | 12/2007 | McKenzie et al. |
| 2007/0293873 A1 | 12/2007 | Chang |
| 2008/0021412 A1 | 1/2008 | Dos Santos et al. |
| 2008/0021413 A1 | 1/2008 | Dos Santos et al. |
| 2008/0021419 A1 | 1/2008 | Dacquay et al. |
| 2008/0021438 A1 | 1/2008 | Dacquay et al. |
| 2008/0033351 A1 | 2/2008 | Trogden et al. |
| 2008/0071246 A1 | 3/2008 | Nazzaro et al. |
| 2008/0082121 A1 | 4/2008 | Chu |
| 2009/0105749 A1* | 4/2009 | de Juan .............. A61F 9/00772 606/206 |
| 2009/0131953 A1 | 5/2009 | Quintin et al. |
| 2010/0298807 A1 | 11/2010 | Jansen et al. |

FOREIGN PATENT DOCUMENTS

| | | |
|---|---|---|
| JP | 2001/0068277 | 3/2001 |
| JP | 2001/0516270 | 9/2001 |
| JP | 2002/0532209 | 10/2002 |
| JP | 2003/0230707 | 8/2003 |
| JP | 2005/0533619 | 11/2005 |
| JP | 2008/0528085 | 7/2008 |
| JP | 2008/0528088 | 7/2008 |
| WO | WO 99/33512 | 7/1999 |
| WO | WO 99/37247 | 7/1999 |
| WO | WO 99/53991 | 10/1999 |
| WO | WO 99/59668 | 11/1999 |
| WO | WO 01/41685 | 6/2001 |
| WO | WO 03/022174 | 3/2003 |
| WO | WO 03/035136 | 5/2003 |
| WO | WO 2004/073765 | 9/2004 |
| WO | WO 2005/023154 | 3/2005 |
| WO | WO 2006/077250 | 7/2006 |
| WO | WO 2006/077349 | 7/2006 |
| WO | WO 2007/024369 | 3/2007 |

OTHER PUBLICATIONS

International Preliminary Report on Patentability of the International Searching Authority for International Application No. PCT/US2008/082735.
International Preliminary Report on Patentability, PCT/US2008/082735, filed Nov. 7, 2008, report dated May 11, 2010.
Supplementary European Search Report, EU App. No. 08846561, filed Nov. 7, 2008, search completed Nov. 26, 2012.
Communication for EU App. No. 08846561, filed Nov. 7, 2008, communication dated Jul. 24, 2013.
JP 2010533258, filed Nov. 7, 2008 Office Action dated Mar. 7, 2013.
CA 2705239, filed Nov. 7, 2008, Office Action dated Mar. 17, 2015.
Letter from China Patent Agent (H.K.) LTD. dated Mar. 23, 2012 and First Office Action for China Patent Application No. 200880124659.0, dated Feb. 15, 2012.
Letter from China Patent Agent (H.K.) LTD dated Dec. 27, 2012 and Second Office Action for China Patent Application No. 200880124659.0 dated Nov. 26, 2012.
Letter from Harrison Goddard Foote LLP dated Jan. 9, 2014 and Communication for EU Application No. 08 846 561.2-1662 dated Jan. 7, 2014.
Official Action for Canada Patent Application 2,705,239 dated Dec. 29, 2015.
Official Action for Canada Patent Application 2,705,239 dated Aug. 4, 2016.

* cited by examiner

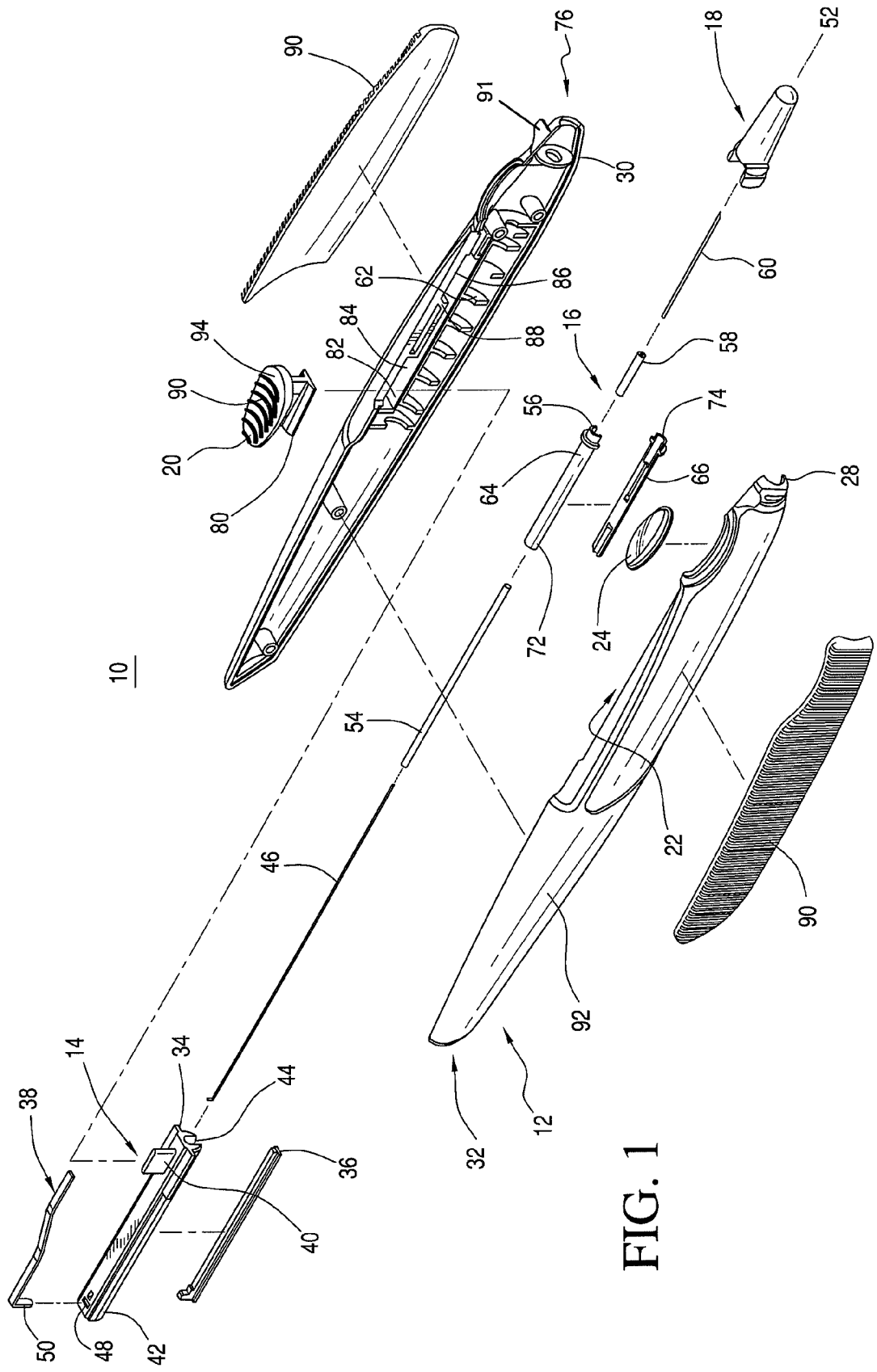

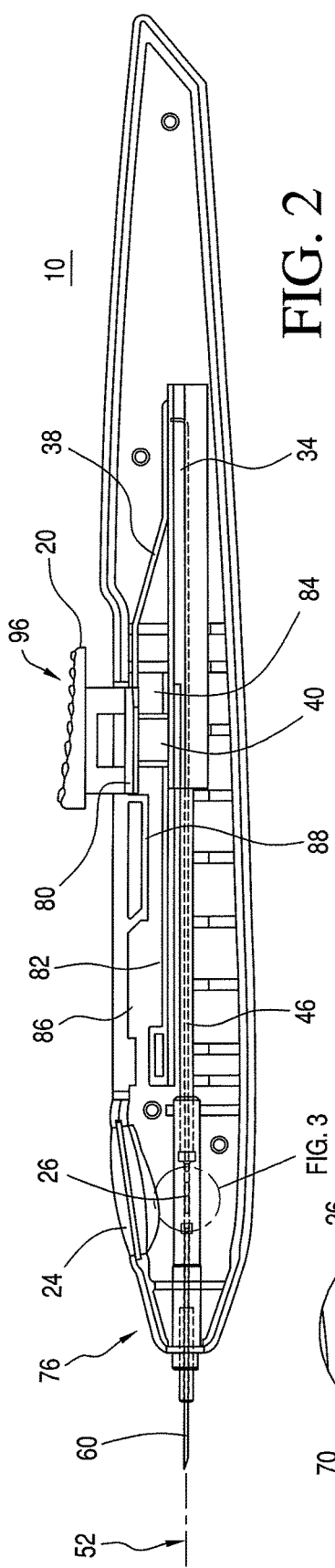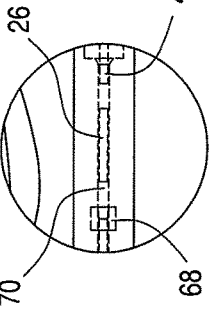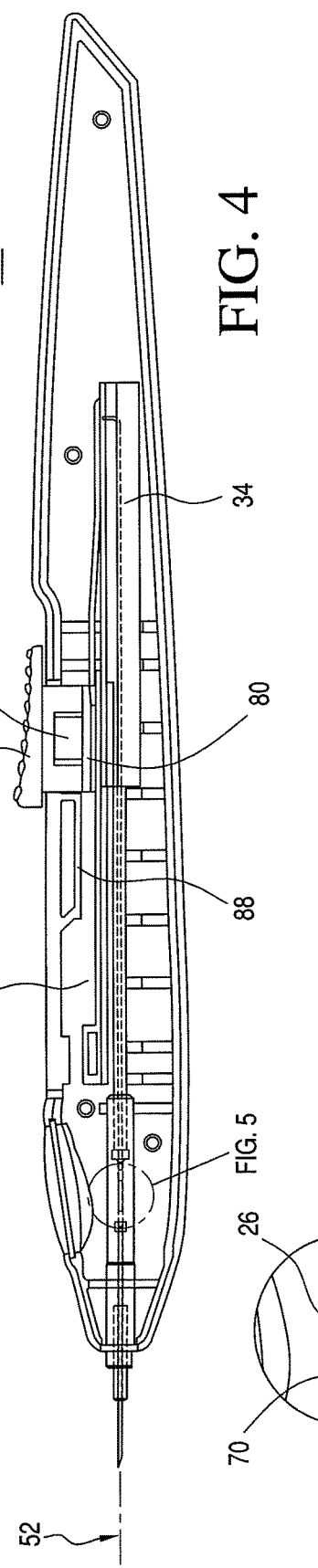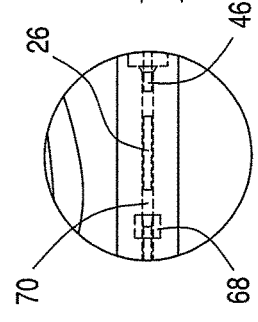

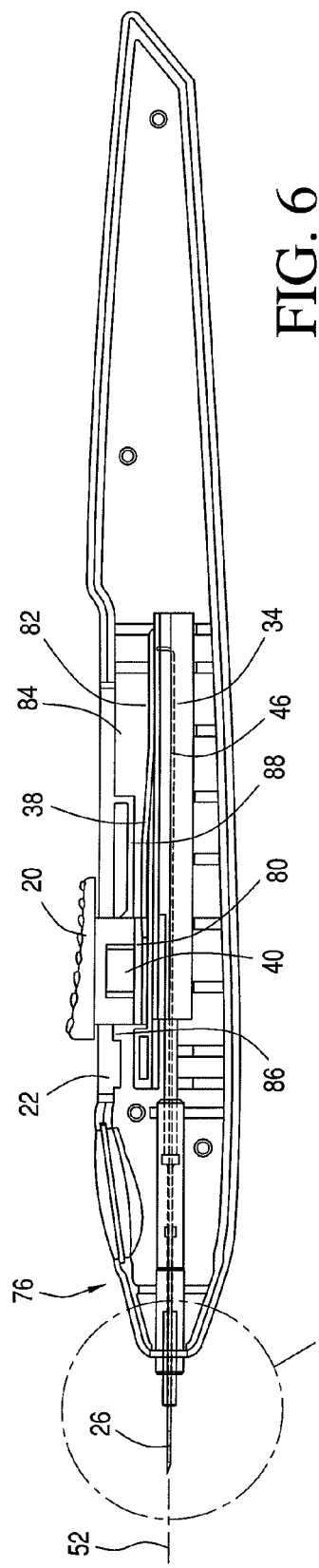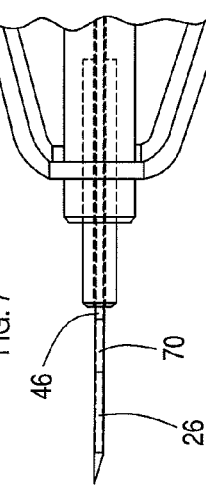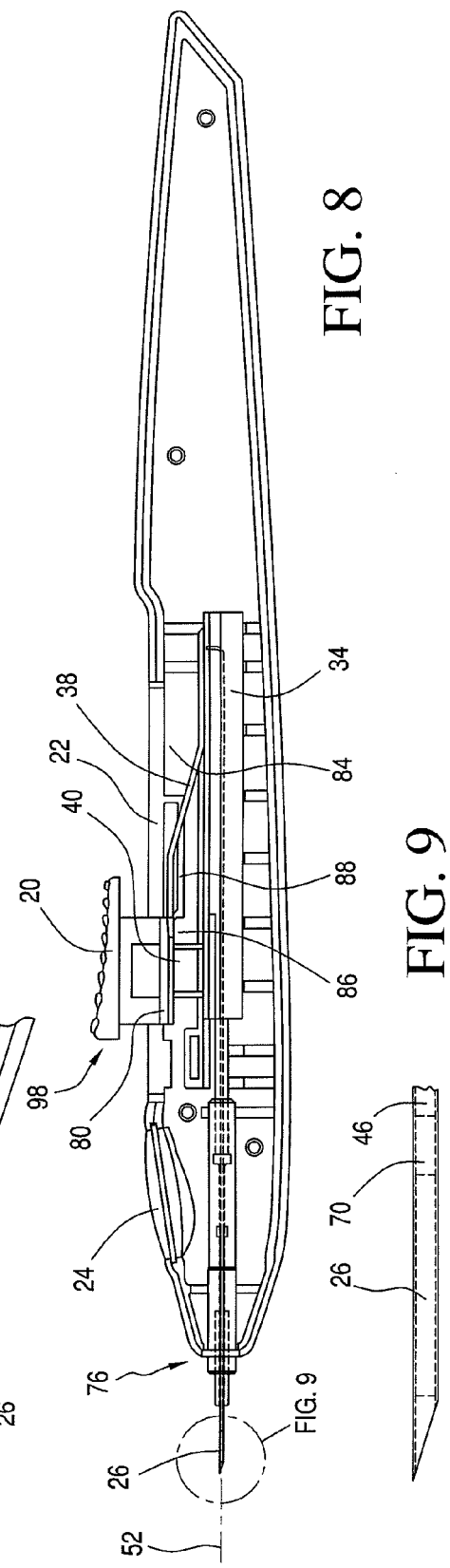

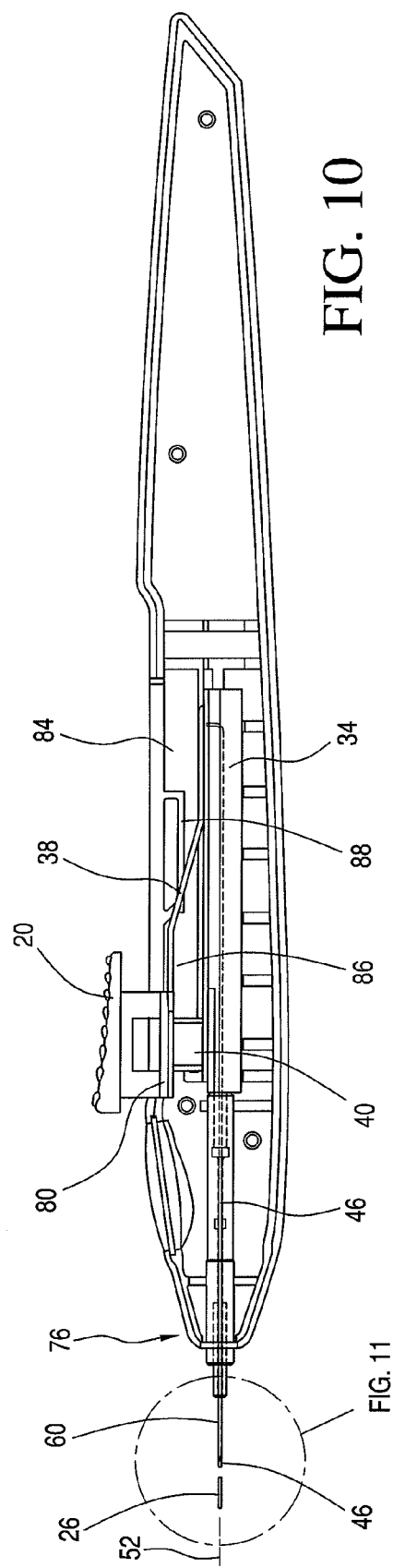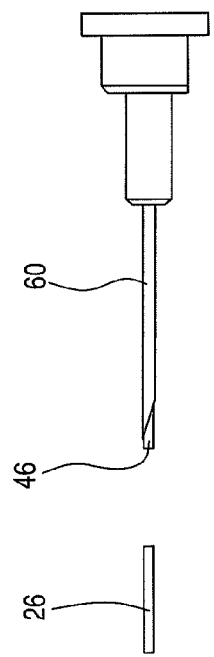

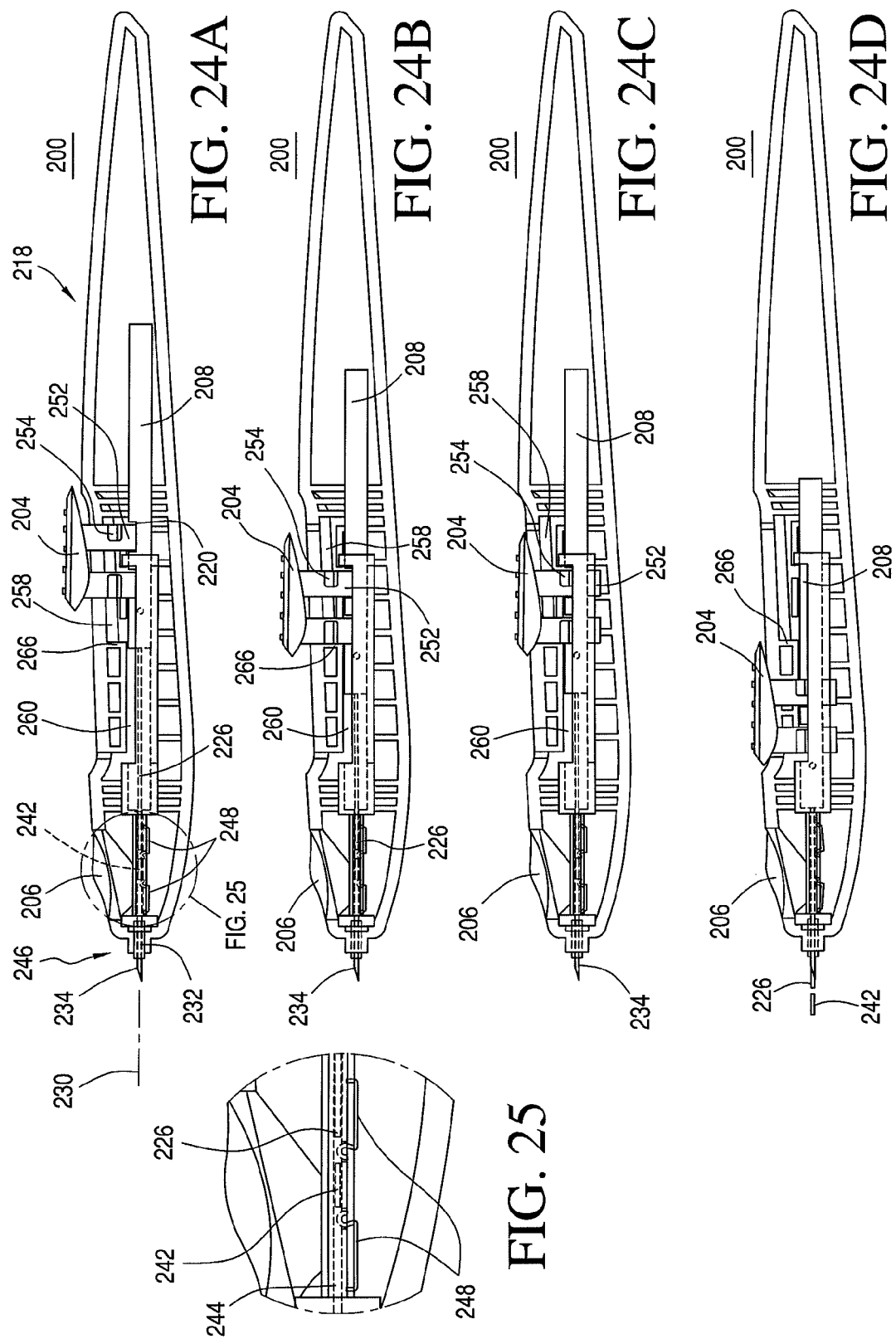

OCULAR IMPLANTATION DEVICE

RELATED APPLICATIONS

The present patent document claims the benefit of the filing date under 35 U.S.C. §119(e) of Provisional U.S. patent application Ser. Nos. 60/986,464, filed Nov. 8, 2007, and 61/075,786, filed Jun. 26, 2008, which are hereby incorporated by reference in their entirety.

FIELD

The invention relates to a device for delivering ocular implants into the vitreous of the eye. Specifically, the invention relates to an ergonomically shaped injector containing a needle capable of puncturing the eye and delivering an implant into the vitreous of the eye.

BACKGROUND

A primary difficulty in treating diseases of the eye is the inability to introduce drugs or therapeutic agents into the eye and maintain these drugs or agents at a therapeutically effective concentration in the eye for the necessary duration. Systemic administration may not be an ideal solution because, often, unacceptably high levels of systemic dosing are needed to achieve effective intraocular concentrations thus increasing the incidence of unacceptable side effects of the drugs. Simple ocular instillation or application is not an acceptable alternative in many cases because the drug may be quickly washed out by tear-action or may otherwise be depleted from the eye into the general circulation. Suprachoroidal injections of drug solutions have been performed, but again the drug availability is short-lived. In summary, available methods make it difficult to maintain therapeutic levels of drug for adequate time periods.

Efforts to address this problem have lead to the development of drug delivery devices, or implants, which can be implanted into the eye such that a controlled amount of desired drug can be released constantly over a period of several days, weeks, or even months. Many such devices have been previously reported. See, for example, U.S. Pat. No. 4,853,224, which discloses biocompatible implants for introduction into an anterior segment or a posterior segment of an eye for the treatment of an ocular condition. In addition, U.S. Pat. No. 5,164,188 discloses a method of treating an ocular condition by introduction of a biodegradable implant comprising drugs of interest into the suprachoroidal space or pars plana of the eye. See also U.S. Pat. Nos. 5,824,072; 5,476,511; 4,997,652; 4,959,217; 4,668, 506; and 4,144,317. Other methods include anchoring a plug or tack containing a drug into the sclera of the eye (see, e.g., U.S. Pat. No. 5,466,233).

Various sites exist in the eye for implantation of a drug delivery device or implant, such as the vitreous of the eye, anterior or posterior chambers of the eye, or other areas of the eye including intraretinal, subretinal, intrachoroidal, suprachoroidal, intrascleral, episcleral, subconjunctival, intracorneal or epicorneal spaces. Wherever the desired location of implantation, typical methods of implantation all require relatively invasive surgical procedures, pose a risk of excessive trauma to the eye, and require excessive handling of the implant. For example, in a typical method for placement in the vitreous, an incision is made through the sclera, and the implant is inserted into and deposited at the desired location in the vitreous, using forceps or other like manual grasping device. Once deposited, the forceps (or grasping device) is removed, and the incision is sutured closed. Alternatively, an incision can be made through the sclera, a trocar can be advanced through the incision and then the implant can be delivered through the trocar. Similar methods can be employed to deliver implants to other locations, e.g., implantation in the anterior chamber of the eye through an incision in the cornea.

There are numerous drawbacks of such techniques for implant delivery. Extensive handling of the implant is necessitated in these techniques, creating a risk that the implant will be damaged in the process. Many implants are polymer-based and are relatively fragile. If portions of the implants are damaged and broken-off, the effective therapeutic dose delivered by the implant once placed will be significantly altered. In addition, it becomes inherently difficult using these methods to achieve reproducible placement from patient to patient. Additionally, all of these techniques require an incision or puncture in the eye large enough to require suturing. Thus such techniques are typically performed in a surgical setting.

Many considerations affect the design and efficacy of an implant delivery device. First, it is important to ensure that the implant is consistently delivered to the subject with each application. Second, because implant therapy often requires numerous applications, the cost of providing the implant should also be considered.

Based on the foregoing, a need for a more facile, convenient, less invasive, and less traumatic means for delivering implants into the eye remains. In addition, a need for a more controlled means of delivering implants into the eye also remains.

BRIEF SUMMARY

The present invention is directed to a device and method for delivering ocular implants to desired locations in the eye. The device comprises a housing having an actuator that is communicatively linked to a plunger. A force applied to the actuator in a direction parallel to the longitudinal axis of the housing is used to deliver the implant to the desired location of the eye. Prior to delivery of the implant, the status of the implant is visually observable to a user.

In an aspect of the invention, an ocular implantation device comprises a housing having a longitudinal axis and a needle extending from the housing, wherein a lumen of the needle is configured to receive an implant. The device further comprises a plunger longitudinally disposed within the housing and a longitudinally extending rod operatively coupled thereto. The plunger and the rod are collectively, translationally moveable along the longitudinal axis of the housing. The rod is configured to be receivable within at least a portion of the lumen. The device also comprises an actuator configured for controlled, guided movement, such movement being controlled and guided by a user and by a portion of the housing. The actuator is operatively engaged with the plunger such that movement of the actuator in a direction aligned with the longitudinal axis of the housing results in translational movement of the plunger and the rod along the longitudinal axis of the housing. Further, the actuator is capable of movement in a direction normal to the longitudinal axis of the housing that does not result in movement of the plunger and the rod.

In another aspect of the invention, an ocular implantation device comprises a housing having a longitudinal axis and a needle extending longitudinally from the housing, with the needle having a lumen extending therethrough. The needle lumen is configured to receive an implant. The device further comprises a plunger longitudinally positioned within the housing and a rod extending therefrom. The plunger and the rod are translationally moveable along the longitudinal axis of the housing from an initial position, and the rod is receivable within at least a portion of the needle lumen. The device also comprises a guide shaft that is fixedly positioned within the housing in communication with the needle, with the guide shaft cooperatively receiving the plunger and the rod upon translational movement thereof and an actuator communicatively linked to the plunger. The actuator is longitudinally moveable from a first position relative to the housing upon application to the actuator of a force aligned with the longitudinal axis of the housing. Movement of the actuator corresponds with translational movement of the plunger from the initial position. The housing has a window disposed therein for visually determining the status of an implant disposed in the housing.

BRIEF DESCRIPTION OF THE DRAWINGS

FIG. 1 is an exploded view of an ocular implantation device in accordance with an embodiment of the present invention.

FIG. 2 is a side elevational view of the ocular implantation device of FIG. 1 in an initial operational configuration with the left housing portion removed to better show internal components thereof.

FIG. 3 is a magnified partial view of FIG. 2 showing the implant in detail.

FIG. 4 is a side elevational view of the ocular implantation device of FIG. 1 in a subsequent operational configuration with the left housing portion removed to better show internal components thereof.

FIG. 5 is a magnified partial view of FIG. 4 showing the implant in detail.

FIG. 6 is a side elevational view of the ocular implantation device of FIG. 1 in another subsequent operational configuration with the left housing portion removed to better show internal components thereof.

FIG. 7 is a magnified partial view of FIG. 6 showing the implant in detail.

FIG. 8 is a side elevational view of the ocular implantation device of FIG. 1 in another subsequent operational configuration with the left housing portion removed to better show internal components thereof.

FIG. 9 is a magnified partial view of FIG. 8 showing the implant in detail.

FIG. 10 is a side elevational view of the ocular implantation device of FIG. 1 in another subsequent operational configuration with the left housing portion removed to better show internal components thereof.

FIG. 11 is a magnified partial view of FIG. 10 showing the implant in detail.

FIGS. 24A-D are side elevational views of the ocular implantation device of FIG. 23 in various stages of operation, with the left housing portion removed to better show internal components thereof.

FIG. 25 is a magnified partial view of FIG. 24A showing the implant in detail.

DETAILED DESCRIPTION

Figure 12:
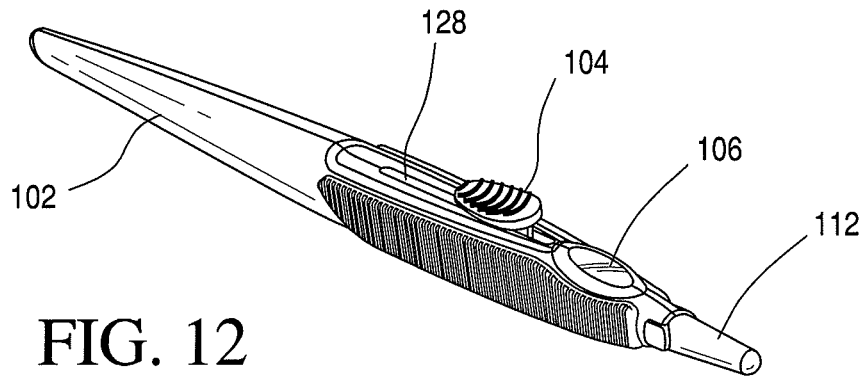
FIGS. 12-17 are perspective views of the ocular implantation device in accordance with alternative embodiments thereof.
Figure 13:
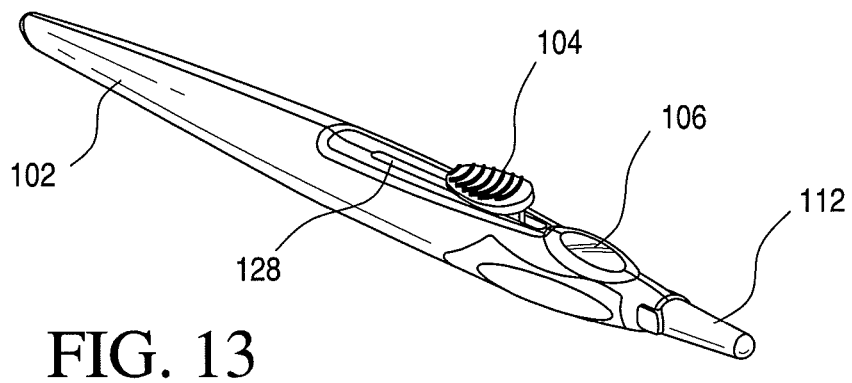
Figure 14:
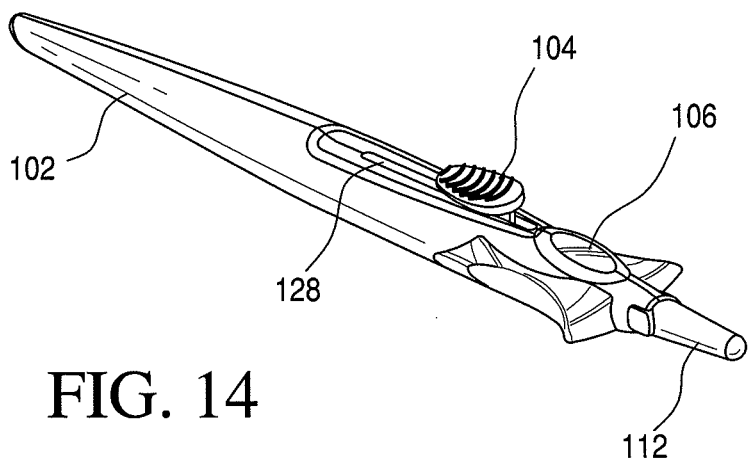
Figure 15:
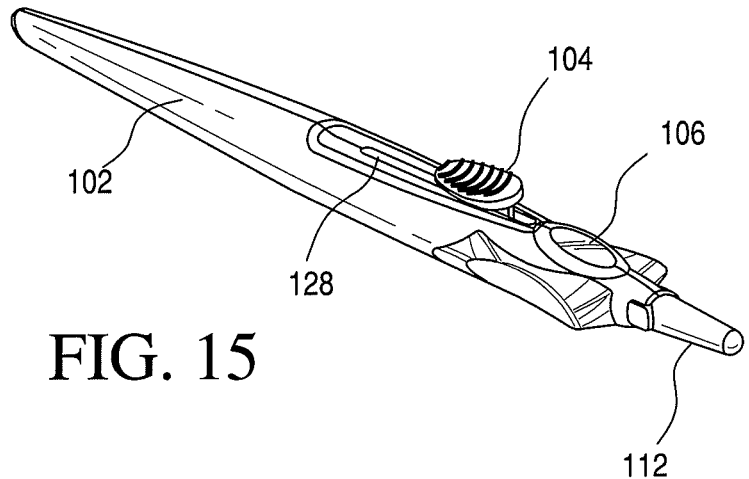
Figure 16:
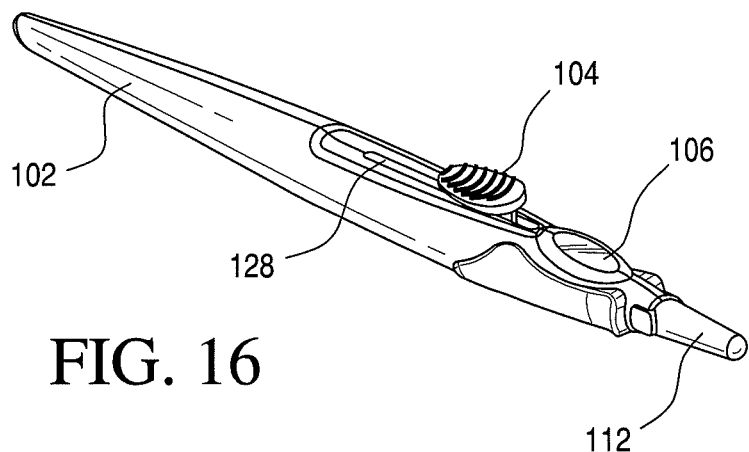
Figure 17:
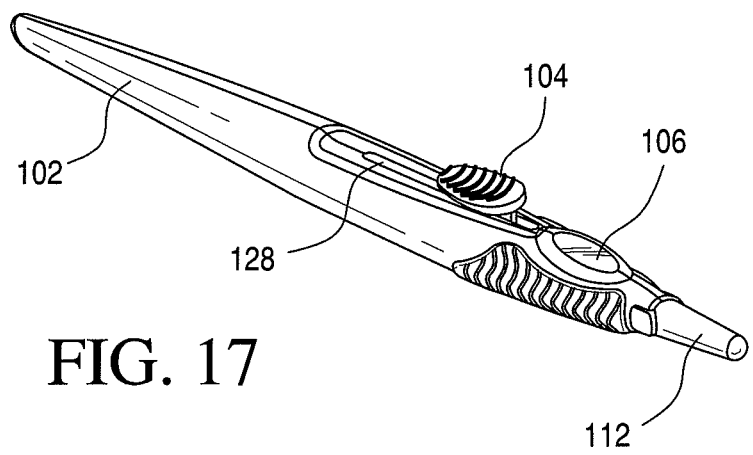

An ocular implantation device is disclosed that provides a user a visual indication of the status of an implant to be delivered to a target tissue prior to delivery. The device further provides a tactile indication of the status of the implant to be delivered prior to delivery.

As used herein, the term "implants" refers to ocular implants or drug delivery devices that can be implanted into any number of locations in the eye and that may release a controlled amount of a bioactive agent or therapeutic immediately or over time. The term implants may include micro-implants that have a sufficiently small cross-sectional area that they can be delivered by methods and/or using devices according to the invention that result in self-sealing of the eye at the puncture site associated with the delivery.

Although many implantable devices may be suitable for use with the ocular implantation device disclosed herein, devices having a tube shape, such as those described in U.S. Pat. No. 6,375,972, the subject matter of which is incorporated herein in its entirety, are preferred. An example of a tube shaped device includes a polyimide tube with a drug core contained therein. The drug core may be made by intermixing polyvinyl alcohol (PVA) with a drug substance such as fluocinolone acetonide. The core may be injected as a slurry into the tube and heated to crosslink the PVA. The tube may be cut to an appropriate length before or after insertion of the drug core. At each end of the tube, a drug permeable coating, for example, PVA may be applied. Alternatively, a permeable coating may be used at one end and an impermeable member may be placed at the other for a reduced rate of release.

As used herein, "self-sealing" methods of delivering implants into the eye refers to methods of introducing implants through a needle and into target tissue of a patient's eye without the need for a suture, or other similar closure means, at the needle puncture site. Such self-sealing methods do not require that the puncture site completely seal immediately upon withdrawal of the needle, but rather that any initial leakage is minimal and dissipates quickly such that a surgeon or another person equally skilled in the art would not be compelled to suture or otherwise provide other similar closure means to the puncture site. It is preferred that all embodiments of the device of the present invention provide self-sealing methods of delivering implants.

Referring now to the drawings, various illustrative embodiments will be described. In the figures herein, an implant is shown preloaded into the various device embodiments for descriptive and explanatory purposes. FIG. 1 depicts an embodiment of the ocular implantation device 10 comprising a housing 12, a plunger assembly 14, a guide shaft assembly 16, and an optional cap 18. The device 10 further comprises an actuator 20 disposed in an elongated housing opening 22 and a transparent window 24 for viewing an implant 26 (perhaps best shown in FIG. 3 or 5) within the housing 12. The housing 12 may comprise a right housing portion 28 and a left housing portion 30, which may be joined together to form the assembled housing 12. The plunger assembly 14 is disposed within the housing 12 at a proximal end 32 thereof when the device 10 is assembled. It comprises a plunger 34, an optional inserter plunger plug 36, and a spring 38. The plunger 34 and the optional inserter plunger plug 36 are configured to fit together. The plunger 34 is longitudinally disposed within the housing 12 and includes a plurality of radial projections 40, a closed end 42, and an open end 44 for receiving a longitudinally extending rod or wire 46. The rod 46 and the plunger 34 are operatively coupled such that movement of the plunger 34 results in movement of the rod 46 thereby resulting in the plunger 34 and the rod 46 being collectively, translationally moveable along the longitudinal axis 52 of the housing 12. An elongated opening or slot 48 is disposed near the closed end 42 of the plunger 34. The spring 38 has a flange portion 50 that may be inserted into the slot 48 of the plunger 34 to enable the spring 38 and the plunger 34 to be operatively connected to one another.

The plunger assembly 14 and the guide shaft assembly 16 are aligned with a longitudinal axis 52 of the housing 12. The guide shaft assembly 16 comprises the rod 46, a guide tube 54, a guide shaft 56, a needle stop 58, and a needle 60 and is disposed within the housing 12 when the housing 12 is assembled. When the device 10 is assembled, the plunger 34 and the rod 46 are translationally moveable along the longitudinal axis 52 of the housing 12 from an initial position, wherein the rod 46 is receivable within at least a portion of a lumen 70 of the needle 60. Additionally, the rod 46 is dimensioned to fit concentrically within the guide tube 54, and the guide tube 54 is dimensioned to fit concentrically within at least a portion of the guide shaft 56. The guide shaft 56 is fixedly positioned within and is supported by the housing 12, in particular by ribs 62 of the housing 12 and is in communication with the needle 60 when the device 10 is assembled. In addition, when the device 10 is assembled, the guide shaft 56 cooperatively receives the plunger 34 and the rod 46 upon translational movement thereof. The guide shaft 56 may include an upper guide shaft portion 64 and a lower guide shaft portion 66, with the lower guide shaft portion 66 optionally including a retention means for preventing the implant 26 from being unintentionally ejected from the device 10 or from being dislodged during shipping. In the exemplary embodiment, the retention means is a core dam 68 (perhaps best shown in FIG. 3 or 5). While the core dam 68 may prevent the implant from being unintentionally dislodged, it does not span the entire travel path of the implant 26. Thus during use of the device 10, the implant 26 may be moved beyond the core dam 68 for ejection from the device 10 by exertion of sufficient force upon the implant 26 by the rod 46.

The window 24 of the housing 12 enables a user to view the implant 26 in the housing 12 prior to its being moved into a lumen 70 (perhaps best shown in FIG. 3 or 5) of the needle 60, which is configured to receive the implant 26. Thus a user may view the implant 26 to ensure that it has not been damaged during shipping and handling or unintentionally ejected. The user may also use the window 24 to ensure that the implant 26 has been moved into the lumen 70 of the needle 60 and thus may be delivered to the target tissue, i.e., a user may look through the window 24 to make sure that the implant 26 is no longer visible and thus has been moved into the lumen 70 of the needle 60.

The guide shaft 56 is preferably open at both ends 72, 74. One end 72 of the guide shaft 56 slidably receives the guide tube 54, and the other end 74 is fitted with the needle stop 58. The needle stop 58 is axially aligned with the rod 46, the guide tube 54, and the guide shaft 56 and is disposed at a distal end 76 of the housing 12 when the device 10 is assembled. The needle stop 58 is configured to receive the needle 60 therethrough such that the needle 60 is positioned within the needle stop 58 and projects from the distal end 76 of the housing 12 when the device 10 is assembled. The needle stop 58 is configured to receive the rod 46 and an implant 26 during operation of the device 10 such that the implant 26 can be driven into the lumen 70 of the needle 60 by the rod 46 during operation. The implant 26 may contain a bioactive agent. The optional cap 18 is frictionally attached to the housing 12 thereby shielding the needle 60 when the device 10 is not being used.

The actuator 20 is preferably positioned partially within the housing 12 and is translationally moveable along the elongated opening 22 in the housing 12. The actuator 20 may be communicatively linked or operatively engaged with the plunger 34 such that movement of the actuator 20 in a direction aligned with the longitudinal axis 52 of the housing 12 results in translational movement of the plunger 34 and the rod 46 along the longitudinal axis 52 of the housing 12. The operative engagement may also enable the actuator 20 to be capable of movement in a direction normal to the longitudinal axis 52 of the housing 12 that does not result in movement of the plunger 34 and the rod 46. For example, the actuator 20 may be operatively engaged with the plunger 34 via one of the radial projections 40 of the plunger 34 and may be coupled to the flat spring 38 such that a force is applied to the actuator 20 by the spring 38.

When the device 10 is assembled, the actuator 20 may be longitudinally moveable from a first position 96 relative to the housing 12 upon application to the actuator 20 of a force aligned with the longitudinal axis 52 of the housing 12. The actuator 20 includes flanges 80 cooperatively engaging a portion of the housing 12 for controlling and guiding movement of the actuator 20. In the exemplary embodiment, the portion of the housing 12 is a track 82 disposed in the housing 12 for controlling and guiding movement of the actuator 20 during operation of the device 10. The track 82 is divided into continuous proximal and distal sections 84, 86 by a protrusion 88 disposed along the track 82. The protrusion 88 aids in preventing inadvertent delivery of the implant 26 by preventing the actuator 20 from accidentally moving along the track 82 from the proximal section 84 to the distal section 86 thereof. Finger gripping means 90 are optionally disposed on an exterior surface 92 of the housing 12 and an upper surface 94 of the actuator 20. The optional finger gripping means 90 aid in secure handling of the device 10 by a user.

Figure 28:
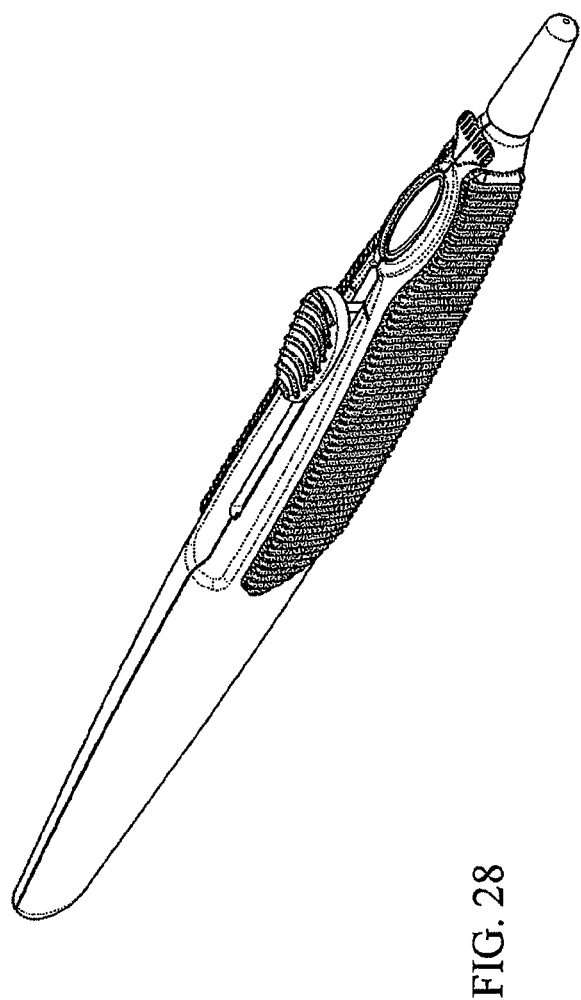
FIG. 28 is a perspective view of an ocular implantation device in accordance with an alternative embodiment of the present invention, which embodiment is similar to the embodiment of FIG. 1.
Figure 29:
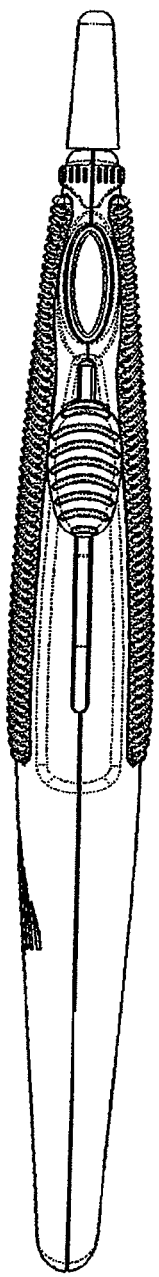
FIG. 29 is a top plan view of the ocular implantation device of FIG. 28.
Figure 30:
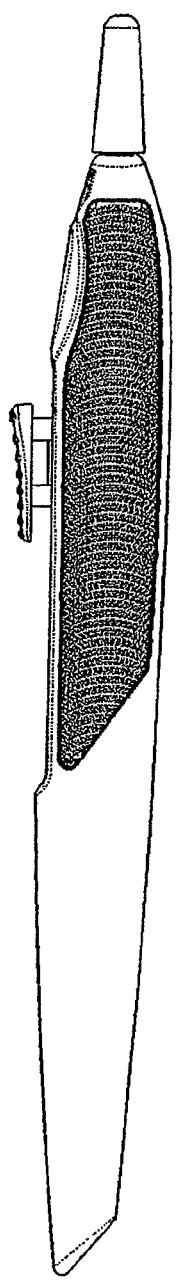
FIG. 30 is a side elevational view of the ocular implantation device of FIG. 28.

The device 10 may further include a gauge or guide member 91 for assessing the location of the site of injection in relation to a landmark on the eye, preferably the limbus. FIGS. 28-30 show an embodiment of the ocular implantation device that is similar to the embodiment of FIG. 1 and that has a slightly different variation of the guide member than the guide member of FIG. 1. Preferably, an outer edge or a sight on the guide member 91 is aligned at or near the landmark, resulting in assessing a site for injection, which would be a predetermined distance from the landmark. Useful distances calibrated from a particular-sized guide member 91 are from about 10 mm to about 0.5 mm. Preferably from about 6 mm to about 2 mm. Most preferably about 4 mm. In the present embodiment, the guide member 91 includes a wing-shaped planar member disposed at the distal end 76 of the housing 12 in horizontal alignment with the longitudinal axis 52 of the housing 12. A user may use the guide member 91 to assist in determining the location of various parts of the eye in relation to one another, e.g., the cornea, the limbus, and the sclera, and in relation to the needle 60 of the device 10 to aid in precisely and accurately injecting the needle 60 into the eye for delivery of the implant 26.

FIGS. 2-11 show the device 10 in progressive stages of operation. In FIG. 2, the device 10 is in an initial configuration, with the actuator 20 positioned partially within the housing 12 at the proximal section 84 of the track 82. In FIG. 2, the actuator 20 is in the first position 96. In the first position 96, the flanges 80 of the actuator 20 are disposed within the housing 12 while much of the remainder of the actuator 20 is disposed exterior to the housing 12. In addition, the actuator flanges 80 are abutting the protrusion 88. Thus in order to move the actuator 20 toward the distal end 76 of the housing 12 thereby delivering the implant 26 to the target tissue, the flanges 80 should clear the protrusion 88. In the initial device configuration, the actuator 20 is acted upon by the flat spring 38 thereby maintaining the actuator 20 in the first position 96. A user may view the implant 26 in the housing 12 when the actuator 20 is in the first position 96, as shown in FIG. 3. Upon application of a downward force generally normal to the actuator 20, flanges 80 of the actuator 20 are vertically displaced below the protrusion 88, as shown in FIG. 4. In this configuration, more of the actuator 20 is disposed within the housing 12 than in the initial configuration shown in FIG. 2. Despite the fact that the actuator 20 moves downwardly relative to the longitudinal axis 52 of the housing 12, the plunger 34, which is operatively coupled to the actuator 20, does not move downwardly relative to the longitudinal axis 52 of the housing 12. In contrast, the plunger 34 remains vertically stationary with respect to the longitudinal axis 52 of the housing 12 throughout use and operation of the device 10. A user may use the window 24 to view the implant 26 in the housing 12 in this configuration, as shown in FIG. 5. As can be seen in FIGS. 3 and 5, the implant 26 is in the same location in the housing 12 when the housing 12 is in its initial configuration, shown in FIG. 2 and the instant configuration, shown in FIG. 4, i.e., movement of the actuator 20 downward relative to the longitudinal axis 52 of the housing 12 does not affect the location of the implant 26 during this stage of operation. As shown in FIG. 6, once the actuator flanges 80 are below the protrusion 88, a force applied to the actuator 20 in the direction of the distal end 76 of the housing 12 that is generally aligned with the longitudinal axis 52 of the housing 12 causes movement of the actuator 20, which causes translational movement of the plunger 34 and the rod 46 from the initial position in the proximal section 84 of the track 82 toward the distal end 76 of the housing 12. As described above, when the actuator 20 is in the first position 96, the track 82 guides movement of the actuator 20 in a direction normal to the longitudinal axis 52 of the housing 12 prior to movement of the actuator 20 in a direction aligned with the longitudinal axis 52 of the housing 12, which results in translational movement of the plunger 24 and the rod 46 along the longitudinal axis 52 of the housing 12.

During operation between the configurations of FIG. 4 and FIG. 6, the implant 26 is contacted by the rod 46, which moves the implant 26 into the lumen 70 of the needle 60 such that the implant 26 is primed for delivery to the target tissue, as can be seen in FIG. 7. The needle 60 may be modified, for example, with indent(s) (not shown) in the lumen 70 of the needle 60 to retain the implant 26 and prevent or eliminate accidental ejection or loss of the implant. After the actuator flanges 80 have cleared the protrusion 88, the spring 38 provides a tactile indication to the user that the implant 26 is primed for ejection as the actuator 20 is forced upwardly in a direction normal to the longitudinal axis 52 of the housing 12 to a second position 98 in the distal section 86 of the track 82 by the force of the spring 38, as shown in FIG. 8. Further, the relative movement, or lack thereof of the implant 26 is observable in the transparent window 24 of housing 12. More particularly, in FIGS. 2 to 5, the implant 26 is observable within the transparent window 24, and in FIGS. 6 to 9, the implant 26 has been driven into the lumen 70 of the needle 60 and is therefore not observable through the transparent window 24, thus indicating to a user that the implant 26 is primed to be delivered. In either event, the transparent window 24 aids in determining the location of the implant 26. The transparent window 24 may contain a magnifying lens. In FIGS. 6-9, the implant 26 is disposed in the lumen 70 of the needle 60 and is ready for ejection into a target site. Once the implant 26 is disposed thusly, a force applied to the actuator 20 that is generally aligned with the longitudinal axis 52 of the housing 12 and in the direction of the distal end 76 of the housing 12 further translates the plunger 34 and the rod 46 through the distal section 86 of the track 82, thereby driving the implant 26 through the lumen 70 of the needle 60 for ejection from the needle 60 and insertion into a target tissue. Thus, when the actuator 20 is in the second position 98, the track 82 guides movement of the actuator 20 in a direction aligned with the longitudinal axis 52 of the housing 12 for further translational movement of the plunger 34 and the rod 46 to deliver the implant 26.

To use the device 10, a user may insert the needle 60 of the device 10, when the device 10 is in the initial configuration shown in FIG. 2, into a subject's eye. In the initial configuration, the user may verify that the implant 26 is disposed in the housing 12 by using the window 24 of the device 10 to view the implant 26. In FIG. 2, the actuator 20 is in the first position 96. The user may apply a downward and a forward force to the actuator 20 to move the actuator 20 and hence the plunger 34 and rod 46 toward the distal end 76 of the housing 12. As described above, the plunger 34 is operatively connected to the rod 46, which drives the implant 26 through the lumen 70 of the needle 60 toward the target site as the actuator 20 is being moving toward the distal end 76 of the housing 12 by the user, ultimately resulting in the implant 26 being ejected from the device 10.

In the first position 96, the actuator 20 is disposed in the proximal section 84 of the track 82 in abutting relation with the protrusion 88. A user may press downwardly on the actuator 20 to move the flanges 80 below the protrusion 88. Once the flanges 80 clear the protrusion 88, a user may press the actuator 20 toward the distal end of the housing 12 thereby moving the actuator flanges 80 beyond the protrusion 88 (FIG. 6). The actuator's movement along the longitudinal axis 52 of the housing 12 causes or translates to similar movement of the plunger 34 and the rod 46 along the longitudinal axis 52 of the housing 12 resulting in the rod 46 pushing the implant 26 into the lumen 70 of the needle 60 thereby priming the implant 26 for ejection. The user may verify that the implant 26 is no longer in the housing 12 by looking through the window 24 of the housing 12. After the user has moved the actuator 20 beyond the protrusion 88, the spring 38 forces the actuator 20 into the second position 98, wherein the actuator 20 is disposed in the distal section 86 of the track 82 with the flanges 80 thereof disposed above the protrusion 88 (FIG. 8). The user may continue to press the actuator 20 toward the distal end 76 of the housing 12 thereby causing further translational movement of the plunger 34 and the rod 46 thus delivering the implant 26 to the target site, as shown in FIGS. 10 to 11. Preferably, the puncture site is self-sealing upon removal of the needle 60.

Figure 18:
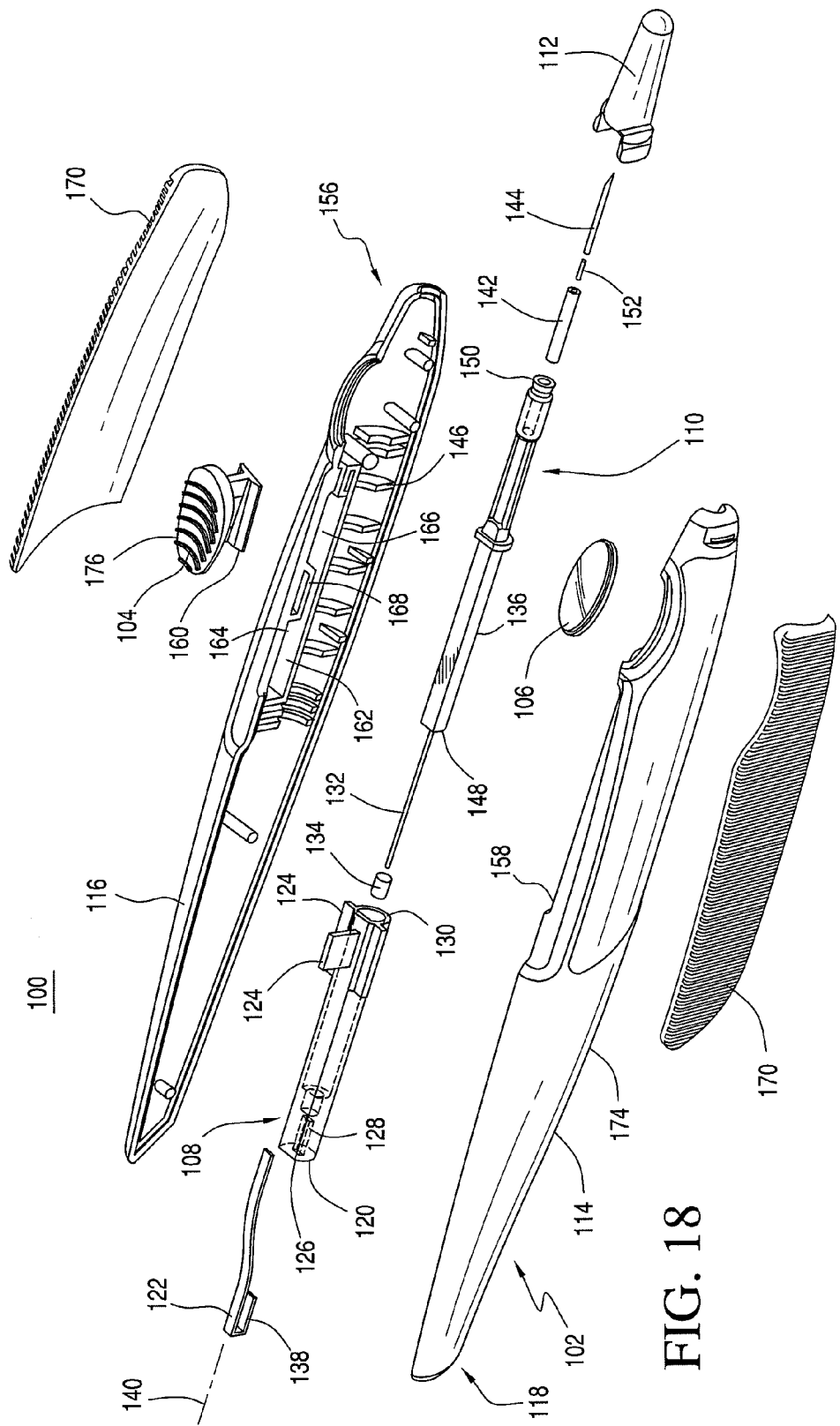
FIG. 18 is an exploded view of an ocular implantation device in accordance with another embodiment of the present invention.
Figure 19:
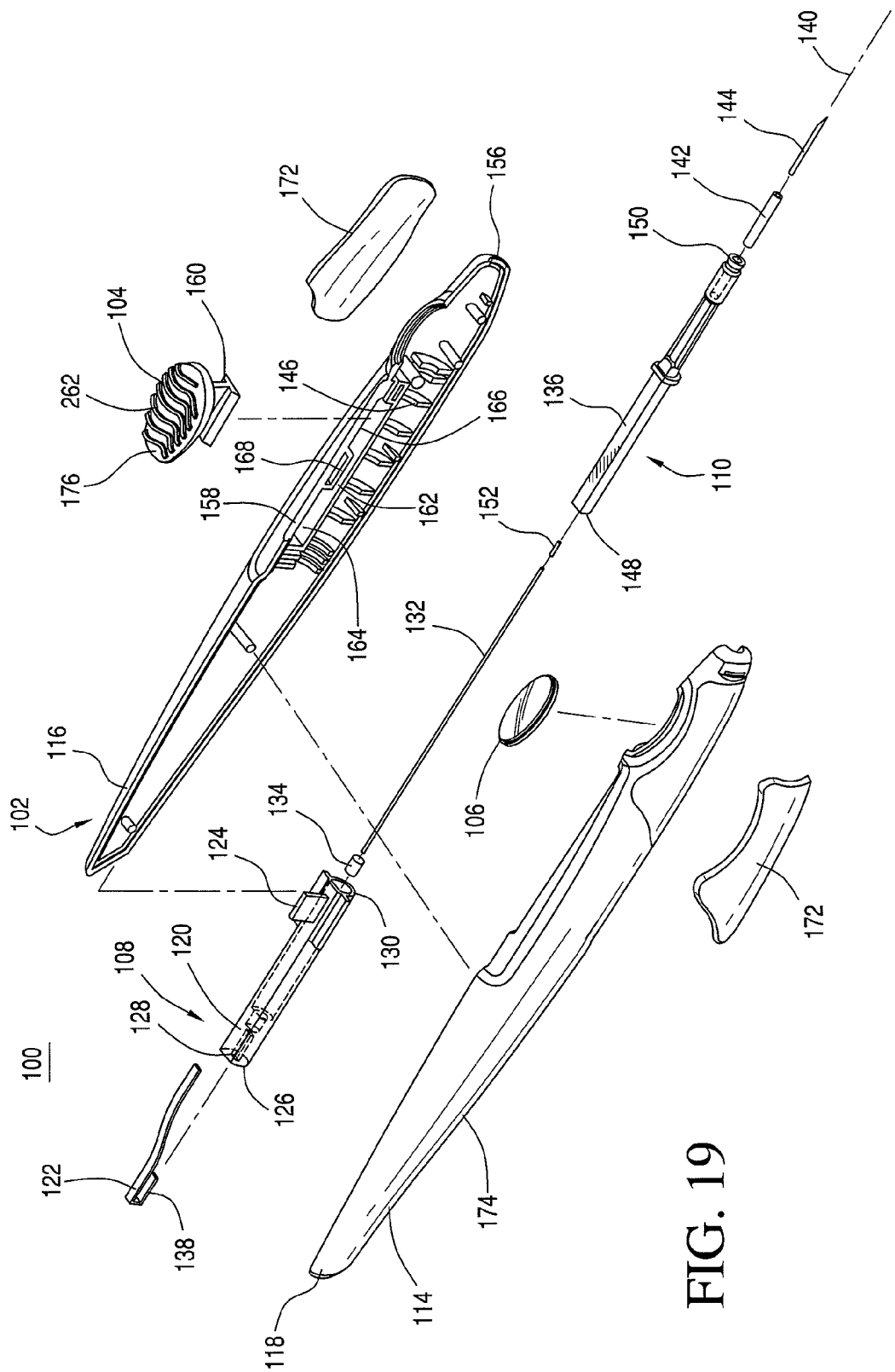
FIG. 19 is an exploded view of an ocular implantation device in accordance with another embodiment of the present invention, which embodiment is similar to the embodiment of FIG. 18.

FIGS. 12-17 are perspective views of the ocular implantation device in accordance with alternative embodiments thereof. Similarly to the embodiment shown in FIG. 1, the ocular implantation devices of FIGS. 12-17 comprise a housing 102, an actuator 104 disposed in an elongated housing opening 128, a transparent window 106 for viewing the implant 26 within the housing 102, and an optional cap 112. Components that are substantially similar to those of the embodiments of FIGS. 18 and 19 are designated with the same reference numerals as used in FIGS. 18 and 19. The devices include various embodiments of finger gripping means optionally disposed on an exterior surface of the housing and an upper surface of the actuator to aid in secure handling of the device by a user.

FIGS. 18 and 19 are exploded perspective views of the ocular implantation device in accordance with alternative embodiments thereof. The devices 100 of FIGS. 18 and 19 are substantially similar; however, the optional finger gripping means 170, 172 present in the two embodiments are somewhat different. FIG. 18 substantially corresponds to the embodiment shown in FIG. 12 and FIG. 19 substantially corresponds to the embodiment shown in FIG. 13. Components that are the same as one another or substantially similar in the devices of FIGS. 18 and 19 share the same reference numeral.

Both embodiments comprise a housing 102, an actuator 104, a window 106, a plunger assembly 108, a guide shaft assembly 110, and an optional cap 112. The housing 102 may comprise a right housing portion 114 and a left housing portion 116, which may be joined together to form the assembled housing 102. The plunger assembly 108 is disposed within the housing 102 at a proximal end 118 thereof when the device 100 is assembled. It comprises a plunger 120 and a spring 122. The plunger 120 includes a plurality of radial projections 124, a closed end 126 having an elongated opening or slot 128 formed therein, and an open end 130 for receiving an extendedly projecting rod or wire 132 and a rod holder 134. In addition, the open end 130 of the plunger 120 is dimensioned to be slidably received by a guide shaft 136 of the guide shaft assembly 110. The spring 122 has a flange portion 138 that may be inserted into the slot 128 of the plunger 120 to enable the spring 122 and the plunger 120 to be operatively connected to one another.

The plunger assembly 108 and the guide shaft assembly 110 are aligned with a longitudinal axis 140 of the housing 102. The guide shaft assembly 110 comprises the rod 132, the rod holder 134, the guide shaft 136, a needle stop 142, and a needle 144 and is disposed within the housing 102 when the housing 102 is assembled. The rod 132 is dimensioned to fit concentrically within the guide shaft 136. The guide shaft 136 is fixedly positioned within and is supported by the housing 102, in particular by ribs 146 of the housing 102.

The guide shaft 136 is preferably open at both ends 148, 150. One end of the guide shaft 148 slidably receives the plunger 136, and the other end 150 is fitted with the needle stop 142 for accommodating the rod 132 and an implant 152 prior to the implant 152 being moved into a lumen 154 (perhaps best shown in FIG. 21) of the needle 144. The needle stop 142 is axially aligned with the rod 132, the rod holder 134, and the guide shaft 136. The needle 144 is positioned in the needle stop 142 and projects from a distal end 156 of housing 102. The needle stop 142 is configured to receive the rod 132 and the implant 152 during operation of the device 100 such that the implant 152 can be driven into the lumen 154 of the needle 144 by the rod 132 during operation. The implant 152 may contain a bioactive agent. The optional cap 112 is frictionally attached to the housing 102 thereby shielding the needle 144 when the device 100 is not being used.

The actuator 104 is preferably positioned partially within the housing 102 and is translationally moveable along an elongated opening 158 in the housing 102. The actuator 104 may be operatively coupled to the plunger 120 via one of the radial projections 124 and may be coupled to the flat spring 122 such that a force is applied to the actuator 104 by the spring 122. The actuator 104 includes flanges 160 cooperatively engaging a track 162 disposed in the housing 102. The track 162 aids in guiding the actuator 104 during operation of the device 100. In the instant embodiment, the track 162 is divided into continuous proximal and distal sections 164, 166 by a protrusion 168 disposed along the track 162. Finger gripping means 170, 172 are optionally disposed on an exterior surface 174 of the housing 102 and an upper surface 176 of the actuator 104. The optional finger gripping means 170, 172 aid in secure handling of the device 100 by a user. As indicated previously, the finger gripping means 170, 172 of the embodiments shown in FIGS. 18 and 19 differ and thus have different reference numerals.

Figure 20A:
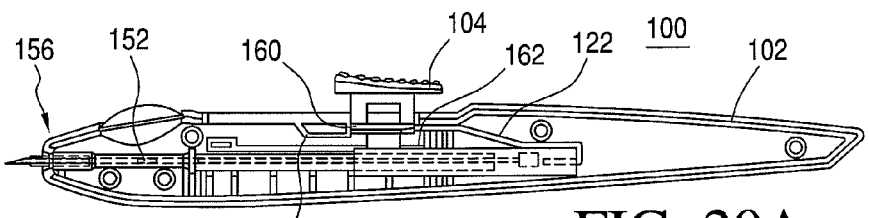
FIGS. 20A-E are side elevational views of the ocular implantation device of FIG. 19 in various stages of operation, with the left housing portion removed to better show internal components thereof.
Figure 20B:
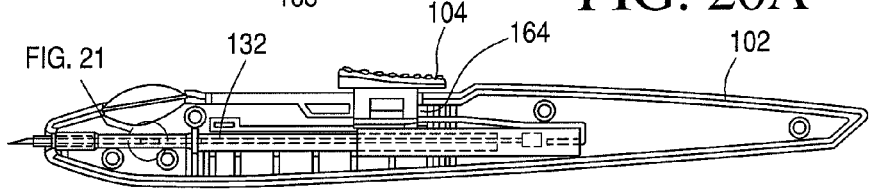
Figure 20C:
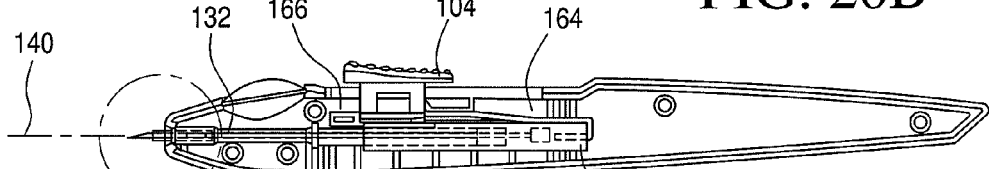
Figure 20D:
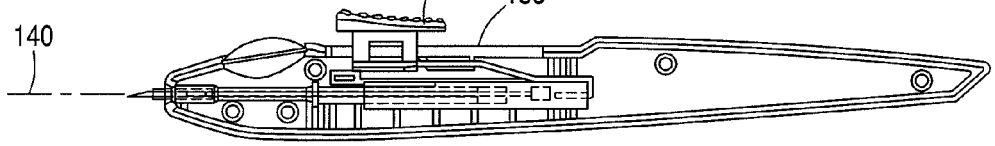
Figure 20E:
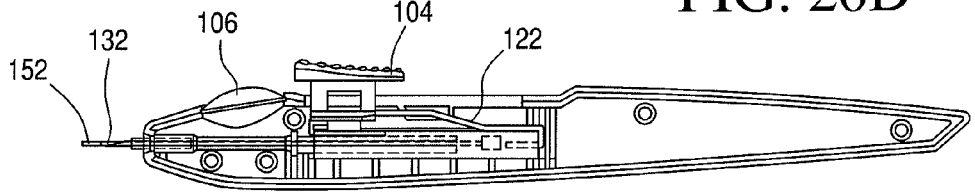
Figure 21:
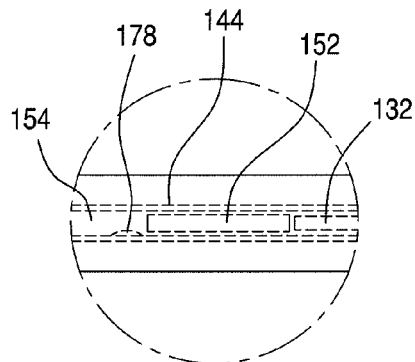
FIG. 21 is a magnified partial view of FIG. 20B showing the implant in detail.
Figure 22:
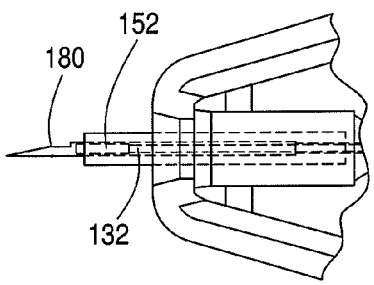
FIG. 22 is a magnified partial view of FIG. 20C showing the implant in detail.

FIGS. 20A-E, 21, and 22 show the device 100 in progressive stages of operation. In FIG. 20A, the device 100 is in an initial configuration, with the actuator 104 positioned partially within the housing 102 in the proximal section 164 of the track 162. In this initial configuration, the actuator 104 is acted upon by the flat spring 122 such that a force is applied to the actuator 104. Upon application of a force that is generally normal to the actuator 104, flanges 160 of the actuator 104 are vertically displaced below the protrusion 168. Upon application of a force that is generally aligned with the longitudinal axis 140 of the housing 102, the actuator 104 is moved from the proximal section 164 of the track 162 toward the distal end 156 of the housing 102 thereby clearing the protrusion 168, as shown in FIG. 20B. During this operation, the implant 152 is contacted by the rod 132, as shown in FIG. 21. An optional retention means 178 may be positioned distally from the implant 152 to prevent movement of the implant 152 during shipping or handling. Once the actuator 104 is beyond the protrusion 168, the implant 152 is primed for ejection by introduction to the lumen 154 of the needle 144, as shown in FIG. 22. The needle 144 may be modified, for example, with indent(s) 180 in the lumen 154 of the needle 144 to retain the implant 152 and prevent or eliminate accidental ejection or loss of the implant 152. In this configuration, the spring 122 provides for a tactile indication to the user that the implant 152 is primed for ejection as the actuator 104 is forced upwardly into the distal section 166 of the track 162 by the applied force of the spring 122. Further, the relative movement, or lack thereof of the implant 152 is observable in the transparent window 106 of housing 102, as shown in FIGS. 21 and 22. The transparent window 106 may contain a magnifying lens. In FIG. 22, the implant 152 is disposed in the lumen 154 of the needle 144 and is ready for ejection into a target site. Once the implant 152 is disposed thusly, a force generally aligned with the longitudinal axis 140 of the housing 102 applied to the actuator 104 causes movement of the actuator 104, which translates to movement of the plunger 120 and rod 132 from the distal section 166 of the track 162, thereby driving the implant 152 through the lumen 154 of needle 144 for ejection from the needle 144 and insertion into a target tissue, as shown in FIG. 20E.

Use of the embodiments of FIGS. 18 to 22 is substantially similar to that of the embodiment of FIGS. 1-11. To use the device 100, a user may insert the needle 144 of the device 100, when the device 100 is in the initial configuration, into a subject's eye. In the initial configuration, the user may verify that the implant 152 is disposed in the housing 102 by looking through the window 106 of the device 100. The user may then apply a downward and then a forward force to the actuator 104 to move the actuator 104 and hence the plunger 120 and rod 132 toward the distal end 156 of the housing 102. As described above, the plunger 120 is operatively connected to the rod 132, which, in turn, pushes the implant 152 through the lumen 154 of the needle 144 toward the target site. Thus, as the actuator 104 is moved toward the distal end 156 of the housing 102 by the user, the implant 152 is being driven through the lumen 154 of the needle 144 until it is ejected from the device 100.

From the initial configuration of FIG. 20A, the actuator 104 initially moves downwardly engaging the proximal section 164 of the track 162 when pressed by the user (FIG. 20B) and then moves toward the distal end 156 of the housing 102 under the protrusion 168 (FIG. 20C). Once the actuator 104 has moved beyond the protrusion 168, the implant 152 is primed for ejection. The user may verify that the implant 152 is no longer in the housing 102 by looking through the window 106 of the housing 102. After the user has moved the actuator 104 beyond the protrusion 168, the spring 122 forces the actuator 104 back up into the distal section 166 of the track 162 (FIG. 20D). The user may continue to press the actuator 104 toward the distal end 156 of the housing 102 to deliver the implant 152 to the target site (FIG. 20E). Preferably, the puncture site is self-sealing upon removal of the needle 144.

Figure 23:
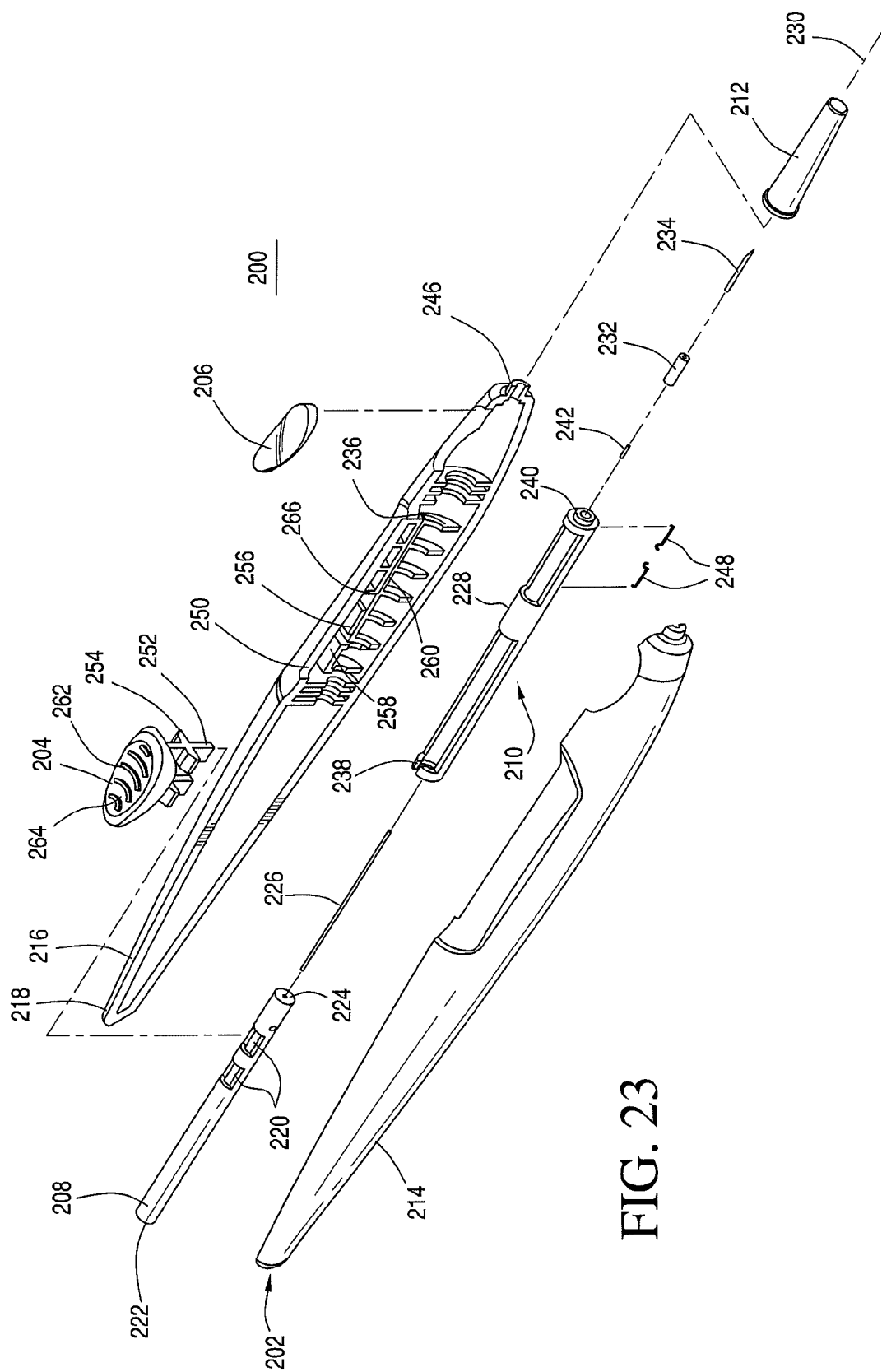
FIG. 23 is an exploded view of an ocular implantation device in accordance with another embodiment of the present invention.

FIGS. 23 to 25 show the ocular implantation device in accordance with another alternative embodiment thereof wherein the actuator includes actuator tabs and the device does not include a spring. FIG. 23 is an exploded perspective view of the device and FIGS. 24A-D and 25 show the device in progressive stages of operation.

The device 200 comprises a housing 202, an actuator 204, a window 206, a plunger 208, a guide shaft assembly 210, and an optional cap 212. The housing 202 may comprise a right housing portion 214 and a left housing portion 216, which may be joined together to form the assembled housing 202. The plunger 208 is disposed within the housing 202 at a proximal end 218 thereof when the device 200 is assembled. The plunger 208 includes plunger openings 220, a closed end 222, and an open end 224 for receiving an extendedly projecting rod or wire 226. In addition, the open end 224 of the plunger 208 is dimensioned to be slidably received by a guide shaft 228.

The plunger 208 and the guide shaft assembly 210 are aligned with a longitudinal axis 230 of the housing 202. The guide shaft assembly 210 comprises the rod 206, the guide shaft 228, a needle stop 232, and a needle 234 and is disposed within the housing 202 when the housing 202 is assembled. The guide shaft 228 is fixedly positioned within and is supported by the housing 202, in particular by ribs 236 of the housing 202, when the device 200 is assembled. The rod 226 is dimensioned to fit concentrically within the guide shaft 228. The guide shaft 228 is preferably open at both ends 238, 240. One end 238 of the guide shaft 228 slidably receives the plunger 208 and the rod 226, and the other end 240 is fitted with the needle stop 232 for accommodating the rod 226 and an implant 242 prior to the implant 242 being moved into a lumen 244 (perhaps best shown in FIG. 25) of the needle 234. The needle stop 232 is axially aligned with the rod 226 and the guide shaft 228. The needle 234 is positioned within the needle stop 232 and projects from a distal end 246 of the housing 202. A retention means 248, shown in FIG. 25, may be disposed in the guide shaft 228 adjacent the implant 242 to prevent movement of the implant 242 during shipping or handling and to prevent inadvertent delivery of the implant 242. The optional cap 212 is frictionally attached to the housing 202 thereby shielding the needle 234 when the device 200 is not being used.

The actuator 204 is preferably positioned partially within the housing 202 and is translationally moveable along an elongated opening 250 in the housing 202. The actuator 204 may be operatively coupled to the plunger 208 via actuator tabs 252 positioned within the plunger openings 220. The actuator tabs 252 enable the actuator 204 to move in directions normal to the longitudinal axis of the housing 202 relative to the plunger 208 while the plunger 208 remains stationary in a plane of motion. The actuator 204 includes flanges 254 cooperatively engaging a track 256 disposed in the housing 202. The track 256 aids in guiding the actuator 204 during operation of the device 200. In the exemplary embodiment, the track 256 is divided into a continuous proximal upper section 258 and distal lower section 260. Because the proximal section 258 of the track 256 is relatively higher in the housing 202 than the distal section 260 of the track 256, an edge wall 266 demarcates the two sections 258, 260 along the track 256. Finger gripping means 262 are optionally disposed on an upper surface 264 of the actuator 204.

Referring to FIGS. 24A-D, in an initial configuration, (shown in FIG. 24A) the actuator 204 is initially positioned toward the proximal end 218 of the housing 202 with the actuator tabs 252 disposed within the plunger openings 220. During use, from the initial configuration, a user applies a force to the actuator 204 in a direction toward the distal end 246 of the housing 202 and generally aligned with the longitudinal axis 230 of the housing 202 causing the actuator 204 to move, which translates to movement of the plunger 208 with the rod 226 extending therefrom toward the distal end 246 of the housing 202. Movement is interrupted as the actuator flanges 254 reach the edge wall 266 of the track, as shown in FIG. 24B. Once the device 200 is in this configuration, the rod 226 is disposed adjacent the implant 242.

From this configuration, a force in a generally normal direction relative to the longitudinal axis 230 of the housing 202 vertically translates the actuator flanges 254 downwardly for engagement with the distal lower track section 260 while the actuator tabs 252 extend through the plunger openings 220, as shown in FIG. 24C. Because the actuator tabs 252 are able to move relative to the plunger openings 220 in directions normal to the longitudinal axis 230 of the housing 202, the plunger 208 remains stationary while the actuator 204 moves downwardly relative to the longitudinal axis 230 of the housing 202. From this configuration, a force applied to the actuator 204 in a direction generally aligned with the longitudinal axis 230 of the housing 202 toward the distal end 246 of the housing 202 causes the rod 226 to urge the implant 242 from the retention means 248 and eject the implant 242 from the lumen 244 of needle 234, as shown in FIG. 24D. This action results in insertion of the implant 242 into the target tissue. As with the previously described embodiments, implant 242 translation or lack thereof may be observed using the transparent window 206.

To use the device 200, a user may insert the needle 234 of the device 200, when the device 200 is in the initial configuration, into a subject's eye. In the initial configuration, the user may verify that the implant 242 is disposed in the housing 202 by looking through the window 206 of the device 200. The user may then apply a forward force to the actuator 204 to move the actuator 204 and hence the plunger 208 and rod 226 toward the distal end 246 of the housing 202. As described above, the plunger 208 is operatively coupled to the rod 226, which, in turn, pushes the implant 242 through the lumen 244 of the needle 234 toward the target site. Thus, as the actuator 204 is moved toward the distal end 246 of the housing 246 by the user, the implant 242 is being driven through the lumen 244 of the needle 234 until it is ejected from the device 200.

From the initial configuration of FIG. 24A, the actuator 204 initially moves toward the distal end 246 of the housing 202 engaging the proximal upper section 258 of the track 256 when pressed by the user. Movement of the actuator 204 is interrupted when the actuator flanges 254 reach the edge wall 266 of the proximal upper track section 258, as shown in FIG. 24B. The user may press downwardly on the actuator 204 to move the actuator flanges 254 into engagement with the distal lower track section 260, as shown in FIG. 24C. The user may then push the actuator 204 toward the distal end 246 of the housing 202 to deliver the implant 242 to the target site (FIG. 24D). The user may verify that the implant 242 is no longer in the housing 202 by looking through the window 206 of the housing 202. Preferably, the puncture site is self-sealing upon removal of the needle 234.

Figure 26:
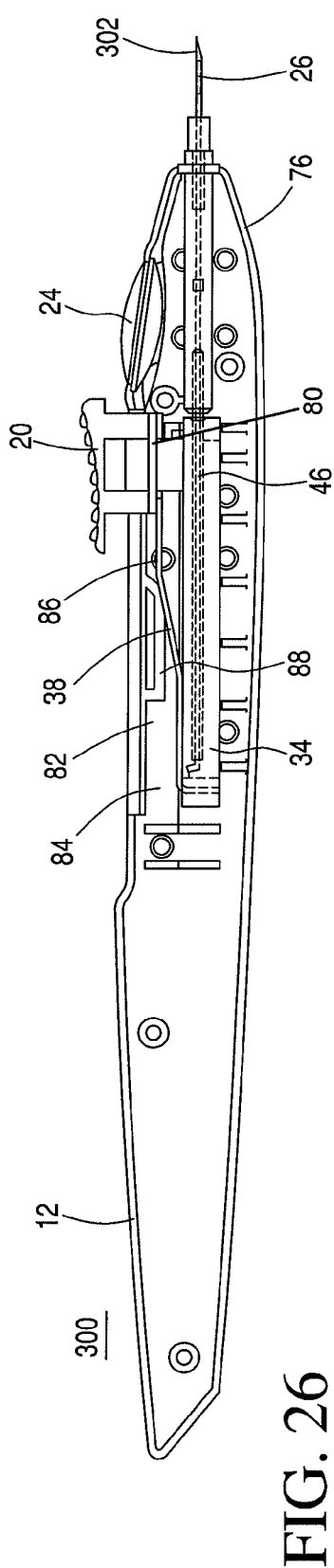
FIGS. 26-27 are side elevational views of an ocular implantation device in accordance with another embodiment of the present invention in various stages of operation, with the right housing portion removed to better show internal components thereof.
Figure 27:
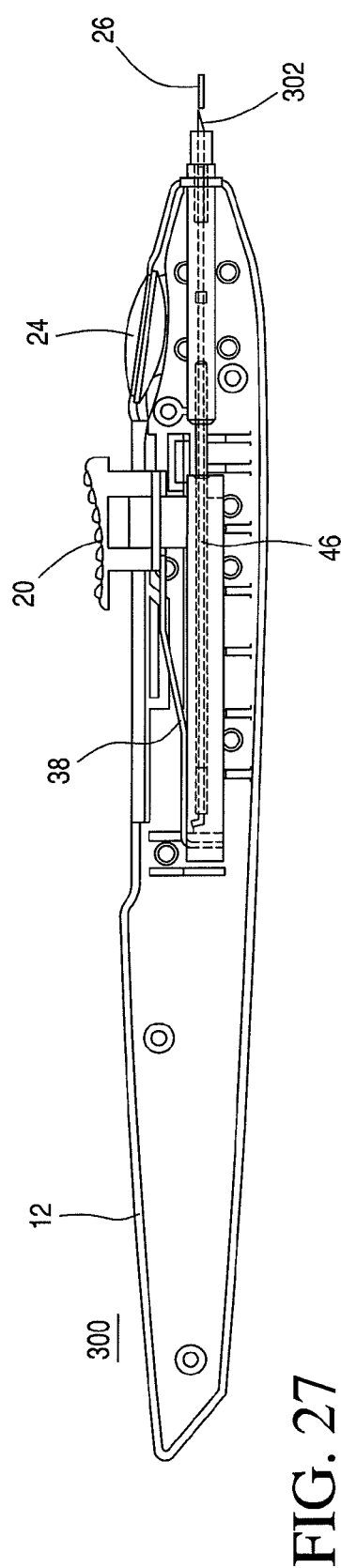

FIGS. 26-27 depict the ocular implantation device in accordance with another alternative embodiment thereof wherein the needle is retractable. These figures show the device 300 in progressive stages of operation. The device 300 of FIGS. 26-27 is structurally similar to the device 10 of FIGS. 1 to 11, thus the same reference numerals will be used to designate components of the instant embodiment that are substantially similar to or the same as those of the embodiment of FIGS. 1 to 11. It will be understood by one of skill in the art that the retractable needle device 300 may have configurations that vary from the configuration shown in FIGS. 26-27. For example, the retractable needle device 300 may be made without a window, may have a simplified track system, or may be made without a rod.

In contrast to the embodiment of FIGS. 1 to 11, the needle 302 of the instant embodiment may be retracted into the distal end 76 of the housing 12. Thus, an implant 26 may be delivered with the instant device 300 by the needle 302 being retracted into the distal end 76 of the housing 12 rather than by the rod 46 pushing the implant 26 completely through the lumen of the needle 60 until it is delivered, as in previously described embodiments.

In FIG. 26, the device 300 is in an initial configuration, wherein the needle 302 is extended from the housing 12 with the implant 26 disposed in the lumen of the needle 302 ready for deployment into a target tissue. A user may apply a force to the actuator 20 that is generally aligned with the longitudinal axis 52 of the housing 12 but is in a direction moving away from the distal end 76 of the housing 12. Movement of the actuator 20 away from the distal end 76 of the housing 12 retracts the needle 60 into the housing 12 thereby deploying the implant 26 into the target tissue, as shown in FIG. 27. The needle 302 simply retracts back into the housing 12 leaving the implant 26 disposed in the target tissue. The retractable needle device 300 is advantageous because it offers control and predictability for the delivery location of an implant. A user may place the needle 302 at the location for desired delivery. When the needle 302 is retracted, the implant is left behind in the location that the needle 302 was in previously. In contrast, in an ocular implantation device embodiment wherein an implant is delivered by being forced out of a needle by a rod, the implant delivery location may be affected by the force with which the rod presses the implant or by the distance from the needle that the rod extends to eject the implant.

To use the device 300, a user may insert the needle 302 into a subject's eye. Then the user may press the actuator 20 away from the distal end 76 of the housing 12 to retract the needle 302 into the housing 12 thereby leaving the implant 26 in the target site (FIG. 27). Preferably, the puncture site is self-sealing upon removal of the needle 302.

The ocular implantation device disclosed herein may be provided as a kit with the implant preloaded into the implantation device. A kit may be provided that includes an implantation device preloaded with an implantable tube including a drug core contained therein with permeable coatings applied to each end of the tube. Alternatively, a kit may be provided that includes an implantation device preloaded with an implantable tube including a drug core contained therein with a permeable coating at one end of the tube and an impermeable member at the other end of the tube. The kit may also include saleable packaging for distribution and sale of the kit. It may further include auxiliary components, including, but not limited to, for example, components for properly disposing of the device, components for assisting in sterilizing an area around the injection site, and/or instructions for using the device.

The above-described ocular implantation device enables a healthcare provider to consistently deliver an implant to a subject. The device further enables the implant to be properly lodged or positioned in the target tissue. Advantageously, the device also ensures that the implant is positioned for delivery immediately prior to or commensurate with entry of the device into the target tissue because the implant is visually observable prior to activating or manipulating the device. The capability to push the actuator forward along the longitudinal axis of the device, with the needle in the subject's target tissue, and to observe that the implant is properly positioned for ejection into the target tissue results in better placement of the implant. Without the ability to visually observe that the implant is properly positioned prior to delivery, it can be difficult or, at the least, time consuming for a user to ensure that the implant has been delivered.

It will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. An ocular implantation device comprising:
   (a) a housing having a longitudinal axis;
   (b) a needle extending from said housing, wherein a lumen of said needle is configured to receive an implant;
   (c) a plunger longitudinally disposed within said housing and a longitudinally extending rod operatively coupled thereto, wherein said plunger and said rod are collectively, translationally moveable along the longitudinal axis of said housing, and wherein said rod is configured to be receivable within at least a portion of the lumen;
   (d) a continuous track disposed within the housing for aiding in controlling and facilitating delivery of the implant, the continuous track having a proximal section and a distal section divided by a protrusion;
   (e) an actuator positioned partially within said housing, the actuator comprising flanges engaged with the continuous track;
   (f) a spring operatively interconnected between said actuator and said plunger;
   (g) a window disposed in said housing for visually determining a status of the implant; and
   (h) a needle stop disposed at a distal end of the housing and axially aligned with the rod, said needle positioned within said needle stop;
   (i) wherein said actuator is operatively engaged with said plunger and with said continuous track,
   wherein movement of said actuator in a direction aligned with the longitudinal axis of said housing results in the translational movement of said plunger and said rod along the longitudinal axis of said housing,
   wherein when said actuator is in a first position in the proximal section of the continuous track, said actuator is in abutting relation with said protrusion and said continuous track guides movement of said actuator in a direction normal to the longitudinal axis of said housing prior to the movement of said actuator in the direction aligned with the longitudinal axis of said housing resulting in the translational movement of said plunger and said rod along the longitudinal axis of said housing, and
   wherein when said actuator is in a second position in the distal section of the continuous track, said continuous track guides the movement of said actuator in the direction aligned with the longitudinal axis of said housing for further translational movement of said plunger and said rod, and
   wherein said protrusion and said continuous track are configured in such a way that the actuator can travel along the continuous track proximal and distal of said protrusion.

2. The ocular implantation device of claim 1, wherein said spring is a flat spring.

3. The ocular implantation device of claim 1, wherein said implant comprises a bioactive agent.

4. The ocular implantation device of claim 3, wherein the bioactive agent is fluocinolone acetonide.

5. The ocular implantation device of claim 1, further comprising retention means for preventing inadvertent delivery or displacement of the implant.

6. The ocular implantation device of claim 5, wherein the retention means is a core dam.

7. The ocular implantation device of claim 1, wherein said window comprises a magnifying lens.

8. A method of delivering an implant to an eye comprising:
   (a) providing the device of claim 1 with said implant preloaded therein;
   (b) inserting said needle of said device into said eye; and
   (c) applying a force to said actuator of said device in order to deliver said implant to said eye.

9. The method of claim 8, further comprising using said window disposed in said housing of said device to determine the status of said implant.

10. A kit for delivering a tube shaped implant to an eye, comprising the device of claim 1 preloaded with the tube shaped implant including a drug core contained therein with permeable coatings applied to each end of a tube of the tube shaped implant.

11. A kit for delivering a tube shaped implant to an eye, comprising the device of claim 1 preloaded with the tube shaped implant including a drug core contained therein with a permeable coating at one end of a tube of the tube shaped implant and an impermeable member at another end of the tube of the tube shaped implant.

12. A method of delivering an implant to an eye comprising:
   (a) providing said device of claim 1 with said implant preloaded therein;
   (b) inserting said needle of said device into said eye; and
   (c) applying a force to said actuator of said device in order to retract said needle of said device thereby delivering said implant to said eye.

13. The ocular implantation device of claim 1, wherein the needle is retractable.

14. An ocular implantation device comprising:
   (a) a housing having a longitudinal axis;
   (b) a needle extending longitudinally from said housing, said needle having a lumen extending therethrough, said lumen configured to receive an implant;
   (c) a plunger longitudinally positioned within said housing and having a rod extending therefrom, wherein said plunger and said rod are translationally moveable along the longitudinal axis of said housing from an initial position, wherein said rod is receivable within at least a portion of said lumen;
   (d) a guide shaft fixedly positioned within and supported by said housing in communication with said needle, said guide shaft cooperatively receiving said plunger and said rod upon the translational movement thereof;
   (e) a guide tube positioned concentrically within at least a portion of the guide shaft, where said rod is dimensioned to fit concentrically within the guide tube;
   (f) a needle stop disposed at a distal end of the housing and axially aligned with the rod, said needle positioned within said needle stop; and
   (g) an actuator communicatively linked to said plunger, said actuator longitudinally moveable from a first position relative to said housing upon application to said actuator of a force aligned with the longitudinal axis of said housing,
   wherein the movement of said actuator in a direction aligned with the longitudinal axis of said housing corresponds with the translational movement of said plunger from said initial position along the longitudinal axis of said housing; and wherein said actuator is capable of movement in a direction normal to the longitudinal axis of said housing that does not result in the translational movement of said plunger and said rod.

15. The ocular implantation device of claim 14, further comprising a window disposed in said housing for visually determining a status of the implant.

* * * * *